United States Patent
Yun et al.

(10) Patent No.: US 11,045,454 B2
(45) Date of Patent: Jun. 29, 2021

(54) METHODS OF TREATING FOOD ALLERGY CONDITIONS

(71) Applicant: Palo Alto Investors LP, Palo Alto, CA (US)

(72) Inventors: Anthony Joonkyoo Yun, Menlo Park, CA (US); Conrad Minkyoo Yun, San Mateo, CA (US)

(73) Assignee: Palo Alto Investors LP, Palo Alto, CA (US)

( * ) Notice: Subject to any disclaimer, the term of this patent is extended or adjusted under 35 U.S.C. 154(b) by 0 days.

(21) Appl. No.: 16/697,670

(22) Filed: Nov. 27, 2019

(65) Prior Publication Data

US 2020/0179349 A1 Jun. 11, 2020

Related U.S. Application Data

(60) Provisional application No. 62/776,081, filed on Dec. 6, 2018.

(51) Int. Cl.
*A61K 31/48* (2006.01)
*A61K 31/437* (2006.01)

(52) U.S. Cl.
CPC .................. *A61K 31/437* (2013.01)

(58) Field of Classification Search
CPC ................ A61K 31/48; A61P 37/08
USPC ........................................ 514/288
See application file for complete search history.

(56) References Cited

U.S. PATENT DOCUMENTS

| 2002/0173505 A1 | 11/2002 | Skogvall |
| 2003/0232855 A1 | 12/2003 | Iwamura et al. |
| 2005/0222270 A1 | 10/2005 | Olney et al. |
| 2010/0016280 A1 | 1/2010 | Nichols et al. |

FOREIGN PATENT DOCUMENTS

| WO | WO0236114 A1 | 5/2002 | |
| WO | WO 2003-026640 A1 * | 4/2003 | ............. A61K 31/22 |

OTHER PUBLICATIONS

Kim, Neuroimmunological Mechanism of Pruritus in Atopic Dermatitis Focused on the Role of Serotonin, Biomolecules & Therapeutics, 2012, vol. 20, No. 6, p. 506-512.
Nau et al., Serotonin 5-HT2 receptor activation prevents allergic asthma in a mouse model, Am J Physiol Lung Cell Mol Physiol, 2015, vol. 308, p. L191-L198.
Phan et al., Systemic Kappa Opioid Receptor Agonists in the Treatment of Chronic Pruritus: A Literature Review, Acta Derm Venereol, 2012, vol. 92, p. 555-560.
Rossi et al., Salvinorin A Inhibits Airway Hyperreactivity Induced by Ovalbumin Sensitization, Frontiers in Pharmacology, 2017, vol. 7, Article 525, p. 1-10.
Szabo, Psychedelics and immunomodulation: novel approaches and therapeutic opportunities, Frontiers in Immunology, 2015, vol. 6, Article 358, p. 1-11.

* cited by examiner

*Primary Examiner* — Charanjit Aulakh
(74) *Attorney, Agent, or Firm* — Bret E. Field; Bozicevic, Field & Francis LLP

(57) ABSTRACT

Methods for treating a subject for a food allergy condition are provided. Aspects of the methods include administering to a subject in need thereof a psychedelic agent in a manner effective to treat the subject for a food allergy condition. Effective administration of a psychedelic agent may include administering the psychedelic agent in an amount effective to treat the subject for the food allergy condition. In some instances, the subject is known to have a food allergy condition.

18 Claims, No Drawings

METHODS OF TREATING FOOD ALLERGY CONDITIONS

CROSS-REFERENCE TO RELATED APPLICATIONS

Pursuant to 35 U.S.C. § 119 (e), this application claims priority to the filing date of U.S. Provisional Patent Application Ser. No. 62/776,081 filed Dec. 6, 2018; the disclosure of which application is herein incorporated by reference.

INTRODUCTION

Numerous reports indicate that the prevalence of food allergy appears to be rising for uncertain reasons. The Centers for Disease Control & Prevention reports that the prevalence of food allergy in children increased by 50 percent between 1997 and 2011 and the prevalence of peanut or tree nut allergy tripled in U.S. children between 1997 and 2008. Each year in the U.S., 200,000 people require emergency medical care for allergic reactions to food.

It is estimated that, in the developed world, food allergy prevalence is currently approaching 10%. The gold standard for food allergy diagnosis is the physician-supervised oral food challenge (OFC). An Australian population-based study of infants using criteria based on OFC, indicated that over 10% of subjects had an allergy to peanut, egg, or sesame. Based on self-reporting rather than OFC, the National Health and Nutrition Examination Survey (NHANES) in the U.S. found the prevalence of food allergy in children to be over 6% from 2007-2010, with the most common food allergens in the study to be milk, peanut, and shellfish. Estimates indicate that 5.9 million children under the age of 18 in the U.S., as many as 1 in 13, have a food allergy. In other developed areas survey and self-reporting studies have seen estimates of similar magnitude, including e.g., 6.7% in Canada and 5.9% in Europe.

Many foods have been reported to cause allergic reactions, including, by some estimates, more than 170 different foods. In the U.S. milk, egg, peanut, tree nuts, wheat, soy, fish and shellfish represent the most common foods to which a subject may be allergic; however, globally sesame allergy is rapidly joining this group of common food allergens. Data indicates that about 40 percent of children with food allergies have experienced a severe allergic reaction such as anaphylaxis. Current interventions for severe reactions include administering epinephrine, which is ideally injected within minutes of the onset of symptoms or even before symptoms appear after a subject ingests a known food allergen.

While some food allergies present during childhood are outgrown by adulthood, many are not and some evidence indicates that the rate at which food allergies are outgrown is, in fact, decreasing. Certain allergens, such as peanuts, tree nuts, fish and shellfish, are well-known to persist into adulthood. Thus, while 5.9 million American children are estimated to have food allergies, when estimates of adult food allergies are included, it is likely that up to 15 million people in the U.S. alone suffer from some form of a food allergy condition.

SUMMARY

Methods for treating a subject for a food allergy condition are provided. Aspects of the methods include administering to a subject in need thereof a psychedelic agent in a manner effective to treat the subject for a food allergy condition. Effective administration of a psychedelic agent may include administering the psychedelic agent in an amount effective to treat the subject for the food allergy condition. In some instances, the subject is known to have a food allergy condition.

DETAILED DESCRIPTION

Methods for treating a subject for a food allergy condition are provided. Aspects of the methods include administering to a subject in need thereof a psychedelic agent in a manner effective to treat the subject for a food allergy condition. Effective administration of a psychedelic agent may include administering the psychedelic agent in an amount effective to treat the subject for the food allergy condition. In some instances, the subject is known to have a food allergy condition.

Before the present invention is described in greater detail, it is to be understood that this invention is not limited to particular embodiments described, as such may, of course, vary. It is also to be understood that the terminology used herein is for the purpose of describing particular embodiments only, and is not intended to be limiting, since the scope of the present invention will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges and are also encompassed within the invention, subject to any specifically excluded limit in the stated range. Where the stated range includes one or both of the limits, ranges excluding either or both of those included limits are also included in the invention.

Certain ranges are presented herein with numerical values being preceded by the term "about." The term "about" is used herein to provide literal support for the exact number that it precedes, as well as a number that is near to or approximately the number that the term precedes. In determining whether a number is near to or approximately a specifically recited number, the near or approximating unrecited number may be a number which, in the context in which it is presented, provides the substantial equivalent of the specifically recited number.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, representative illustrative methods and materials are now described.

All publications and patents cited in this specification are herein incorporated by reference as if each individual publication or patent were specifically and individually indicated to be incorporated by reference and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual publication dates which may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

While the apparatus and method has or will be described for the sake of grammatical fluidity with functional explanations, it is to be expressly understood that the claims, unless expressly formulated under 35 U.S.C. § 112, are not to be construed as necessarily limited in any way by the construction of "means" or "steps" limitations, but are to be accorded the full scope of the meaning and equivalents of the definition provided by the claims under the judicial doctrine of equivalents, and in the case where the claims are expressly formulated under 35 U.S.C. § 112 are to be accorded full statutory equivalents under 35 U.S.C. § 112.

Methods

As summarized above, the present disclosure includes methods of treating a food allergy condition in a subject where aspects of the described methods include administering to a subject in need thereof a psychedelic agent in an amount effective to treat the subject for the food allergy condition.

The subject methods find use in the treatment of a variety of different food allergy conditions. By treatment is meant both a prevention and/or at least an amelioration of the symptoms associated with the condition afflicting the subject is achieved, where amelioration is used in a broad sense to refer to at least a reduction in the magnitude of a parameter, e.g., symptom, associated with the food allergy condition being treated. As such, treatment also includes situations where the condition, or at least symptoms associated therewith, are completely inhibited, e.g. prevented from happening, or stopped, e.g. terminated, such that the subject no longer suffers from the food allergy condition, or at least the symptoms that characterize the condition.

As summarized above, treating a subject for a food allergy condition may include administering to the subject an effective amount a psychedelic agent. The amount of agent constituting an effective amount may vary based on various factors, including but not limited to e.g., the agent or agents administered, the condition to be treated, the desired level of treatment, etc. In some instances, an effective amount may be effective to prevent a symptom associated with the food allergy condition from occurring. e.g., when the subject ingests the allergen. Prevention of a symptom associated with a food allergy may vary and may include e.g., prevention of a mild to moderate symptom (e.g., hives, itchy (especially in the mouth or ear canal), tingling in the mouth, nausea, vomiting, diarrhea, stomach pain, nasal congestion, rhinorrhea, sternutation, slight dry cough, odd taste in mouth, etc.), and/or prevention of moderate to severe symptoms (e.g., trouble swallowing, shortness of breath, wheezing, repetitive cough, cyanosis, hypotension, lightheadedness, disorientation, syncope, loss of consciousness, chest pain, a weak or "thready" pulse, anxiety (e.g., a sense of "impending doom"), anaphylaxis, constriction and tightening of the airways, shock with a sudden hypotension, rapid pulse, dizziness, circulatory collapse, swelling (especially lips, face, tongue and/or throat), abdominal pain, diarrhea, nausea, vomiting, etc.).

In some instances, an effective amount may be effective to reduce the severity of a symptom associated with the food allergy condition from occurring. e.g., when the subject ingests the allergen. Reduction in the severity of a symptom associated with a food allergy may vary and may include e.g., reduction of a mild to moderate symptom (e.g., hives, itchy (especially in the mouth or ear canal), tingling in the mouth, nausea, vomiting, diarrhea, stomach pain, nasal congestion, rhinorrhea, sternutation, slight dry cough, odd taste in mouth, etc.), and/or reduction of moderate to severe symptoms (e.g., trouble swallowing, shortness of breath, wheezing, repetitive cough, cyanosis, hypotension, lightheadedness, disorientation, syncope, loss of consciousness, chest pain, a weak or "thready" pulse, anxiety (e.g., a sense of "impending doom"), anaphylaxis, constriction and tightening of the airways, shock with a sudden hypotension, rapid pulse, dizziness, circulatory collapse, swelling (especially lips, face, tongue and/or throat), abdominal pain, diarrhea, nausea, vomiting, etc.). Symptom reduction may include e.g., a reduction in the magnitude of the symptom, a reduction in the frequency of the symptom, a reduction in the duration of a symptom, and/or combinations thereof.

In some instances, treatment with an effective amount may include, but is not necessarily limited to, complete reduction in one or symptoms of a food allergy condition. In some instances, treatment with an effective amount may include, but is not necessarily limited to, complete prevention in one or symptoms of a food allergy condition. Administration of an effective amount of one or more psychedelic agents may be performed in one or more administrations of the agent(s), including e.g., where the agent is administered in a single dose or where the agent is administered as part of a treatment regimen that includes administration of multiple doses over some period of time.

An amount a psychedelic agent administered or to be administered to a subject may be expressed in terms of effect, relative terms, and/or absolute terms. For example, in some instances an amount of a psychedelic agent administered may range from 15 micrograms (μg) to 800 milligrams (mg) or more.

For example in some instances, an amount of a psychedelic agent administered to a subject may be in the microgram range, including but not limited to e.g., from 15 μg to 1500 μg, from 25 μg to 1500 μg, from 50 μg to 1500 μg, from 75 μg to 1500 μg, from 100 μg to 1500 μg, from 200 μg to 1500 μg, from 300 μg to 1500 μg, from 400 μg to 1500 μg, from 500 μg to 1500 μg, from 600 μg to 1500 μg, from 700 μg to 1500 μg, from 800 μg to 1500 μg, from 900 μg to 1500 μg, from 1000 μg to 1500 μg, from 20 μg to 1000 μg, from 20 μg to 900 μg, from 20 μg to 800 μg, from 20 μg to 700 μg, from 20 μg to 600 μg, from 20 μg to 500 μg, from 20 μg to 400 μg, from 20 μg to 300 μg, from 20 μg to 200 μg, from 20 μg to 100 μg, etc.

In some instances, an amount of a psychedelic agent administered to a subject may be in the milligram range, including but not limited to e.g., from 1 mg to 1000 mg, from 2 mg to 1000 mg, from 3 mg to 1000 mg, from 4 mg to 1000 mg, from 5 mg to 1000 mg, from 10 mg to 1000 mg, from 15 mg to 1000 mg, from 20 mg to 1000 mg, from 30 mg to 1000 mg, from 40 mg to 1000 mg, from 50 mg to 1000 mg, from 75 mg to 1000 mg, from 100 mg to 1000 mg, from 150 mg to 1000 mg, from 200 mg to 1000 mg, from 300 mg to 1000 mg, from 400 mg to 1000 mg, from 500 mg to 1000 mg, from 600 mg to 1000 mg, from 700 mg to 1000 mg, from 800 mg to 1000 mg, from 900 mg to 1000 mg, from 1 mg to 900 mg, from 1 mg to 800 mg, from 1 mg to 700 mg, from 1 mg to 600 mg, from 1 mg to 500 mg, from 1 mg to 450 mg, from 1 mg to 400 mg, from 1 mg to 350 mg, from 1 mg to 300 mg, from 1 mg to 250 mg, from 1 mg to 200 mg, from 1 mg to 175 mg, from 1 mg to 150 mg, from 1 mg to 125 mg, from 1 mg to 100 mg, etc.

In some instances, the amount of a psychedelic agent administered may be a microdose, a threshold dose, a light dose, a common dose, a strong dose, or a heavy dose.

The use of the term "microdose" herein, generally refers to a sub-threshold dose, including e.g., a fraction of a threshold dose, e.g., a fifth of a threshold dose or less, a tenth of a threshold dose or less, etc. Depending on the particular agent employed, a microdose may be less than 100 mg, less than 75 mg, less than 70 mg, less than 60 mg, less than 50 mg, less than 40 mg, less than 30 mg, less than 20 mg, less than 15 mg, less than 10 mg, less than 7.5 mg, less than 5 mg, less than 4 mg, less than 3 mg, less than 2 mg, less than 1 mg, less than 500 µg, less than 300 µg, less than 250 µg, less than 200 µg, less than 125 µg, less than 100 µg, less than 50 µg, less than 30 µg, less than 25 µg, less than 20 µg, or less than 15 µg.

The term "threshold dose" as used herein and generally refers to a dose at which the mental and physical alterations produced by the agent first become apparent, including e.g., where the effects are distinctly beyond that of placebo. Depending on the particular agent employed, a threshold dose may be 100 mg or more, 75 mg or more, 70 mg or more, 60 mg or more, 50 mg or more, 40 mg or more, 30 mg or more, 20 mg or more, 15 mg or more, 10 mg or more, 7.5 mg or more, 5 mg or more, 4 mg or more, 3 mg or more, 2 mg or more, 1 mg or more, 500 µg or more, 300 µg or more, 250 µg or more, 200 µg or more, 125 µg or more, 100 µg or more, 50 µg or more, 30 µg or more, 25 µg or more, 20 µg or more, or 15 µg or more.

The term "light dose" as used herein and generally refers to a dose at which effects are noticeable and clearly distinct from sobriety but remain in the background of the subject's awareness, including e.g., where the effects can be ignored by increasing the focus one directs towards performing a complex task. Depending on the particular agent employed, a light dose may range from 25 µg to 300 mg or more, including but not limited to e.g., 25 µg to 1 mg, 50 µg to 200 mg, 1 mg to 100 mg, 100 mg to 300 mg, etc., including any of exemplary light dose ranges described herein.

The term "common dose" as used herein and generally refers to a dose at which the effects and the nature of a substance is clear and distinct and ignoring the action of the psychedelic agent becomes difficult, including e.g., where the user is generally able to partake in regular behaviors and remain functional and able to communicate but the effects can be allowed to occupy a predominant role in the subject's mind. Depending on the particular agent employed, a common dose may range from less than 60 µg to 500 mg or more, including but not limited to e.g., 100 µg to 10 mg, 500 µg to 250 mg, 10 mg to 400 mg, etc., including any of exemplary common dose ranges described herein.

The term "strong dose" as used herein and generally refers to a dose at which a subject is mostly incapable of functioning, interacting normally, or thinking in a sober manner, including e.g., where the effects of the agent are clear and cannot be ignored by the subject. In some instances, a strong dose may render a subject entirely engaged in a psychedelic experience regardless of whether the subject focuses on the effects of the agent. Depending on the particular agent employed, a strong dose may range from less than 100 µg to 800 mg or more, including but not limited to e.g., 200 µg to 300 mg, 1 mg to 500 mg, 100 mg to 750 mg, etc., including any of exemplary common dose ranges described herein.

The term "heavy dose" as used herein and generally refers to a dose at which the upper limit of the effects the agent is capable of producing, in terms of perceptible characteristic effects, is achieved. In some instances, a subject administered a heavy dose may be rendered incapable of functioning and communicating normally. In some instances, a subject administered a heavy dose may experience side effects not present at lower doses. Depending on the particular agent employed, a heavy dose may range from more than 200 µg, including but not limited to e.g., more than 400 µg, more than 1 mg, more than 1.5 mg, more than 3 mg, more than 10 mg, more than 20 mg, more than 50 mg, more than 100 mg, more than 150 mg, more than 200 mg, more than 300 mg, more than 500 mg, more than 800 mg, etc., including any of exemplary common dose ranges described herein.

The term "overdose" as used herein and generally refers to a dose at which greater than recommended, intended or generally practiced, with the possibility of the dose resulting in serious injury or death. Depending on the particular agent employed, an overdose will generally be a dosage above any commonly appreciated heavy dose.

In some embodiments, an effective amount of a psychedelic agent may be administered in a psychoactive amount of the psychedelic agent. As used herein, the terms "psychoactive amount" and "psychoactive dose" are used interchangeably and generally refer to an amount sufficient to produce psychoactive effects in a subject. Depending on the particular agent employed, psychoactive amounts will vary and will generally include doses at or above a threshold dose and below an overdose, including but not limited to e.g., a dose at a threshold dose, a dose above a threshold dose, a light dose, a dose above a light dose, a common dose, a dose above a common dose, a strong dose, a dose above a strong dose, or a heavy dose. A psychoactive amount of a psychedelic agent will generally exclude low dosages that do not, or are intended not to, produce psychedelic effects, such as but not limited to e.g., microdosages, sub-threshold dosages, non-psychoactive amounts, and the like.

Methods according to certain embodiments include administering according to a treatment protocol and/or determining a treatment protocol for a subject having a food allergy condition, including e.g., a treatment protocol for a predicted adverse response to a food allergen. A "treatment protocol" for a subject having a food allergy condition is a course of one or more actions which are taken to alleviate the condition or symptoms of the condition in the subject. The course of one or more actions which are taken to alleviate the condition or symptoms of the condition may include administering a psychedelic agent, including where the psychedelic agent is administered according to a course of treatment, administered according to one or more of the dosages described herein, combinations thereof, and the like. Courses of treatment may be predetermined or based on one or more measured parameters of the subject. The course of one or more actions which are taken to alleviate the condition or symptoms of the condition may include, in some instances, at least a period of inaction or not taking immediate action to treat the condition.

In some instances, a course of treatment or therapeutic regimen employed may include a holiday period. A "holiday period", as used herein, will generally refer to a period of time during which the subject is not administered a psychedelic agent. The duration of this period between psychedelic agent administration, may vary, but in certain embodiments is 1 hour or longer, e.g., 2 hours or longer, including 3 hours or longer, e.g., 6 hours or longer, 12 hours or longer, 1 day or longer, such as 2 days or longer, including 5 days or longer, 10 days or longer, 15 days, or longer. As such, embodiments of the methods include non-chronic (i.e., non-continuous) administration of the psychedelic agent. In other embodiments a psychedelic agent may be administered chronically.

A treatment regimen including non-chronic administration of the psychedelic agent may include a pre-determined treatment schedule, including e.g., a schedule of multiple therapies set out over a period of time, including hours, days, weeks, months, years, etc. Such "multiple therapies" may include e.g., multiple doses of psychedelic agents (including where the doses include the same or different psychedelic agents); one or more doses of psychedelic agent with an additional non-psychedelic therapy, such as but not limited to e.g., oral tolerance therapy, oral immunotherapy, psychiatric therapy, and the like; combinations thereof, etc.

In some embodiments, a treatment regimen including non-chronic administration of the psychedelic agent may include an element of randomness. For example, in some instances, psychedelic agent may be administered in an "irregularly irregular" manner. In some instances, a holiday period may be administered in an "irregularly irregular" manner. As such, duration of the psychedelic agent administration, frequency of psychedelic agent administration, as well as duration and/or frequency of holiday periods between such events, may vary randomly over at least a portion of, including the entire, course of a treatment. Such variation may not follow any pattern, but is instead random. The duration of a treatment regimen including an element of randomness may be predetermined or determined by some measured outcome, including e.g., where a subject's food allergy condition to treated to a desired extent.

In some instances, methods of the present disclosure may include an antigen challenge. As used herein, the term "antigen challenge" generally refers to exposing a subject to an antigen to which the subject may have an allergy. The subject may be known to have an allergy to the antigen or the subject may be suspected of having an allergy to the antigen. With respect to food allergies, such an antigen challenge may be performed as an oral food challenge (OFC). In an OFC, a subject may be administered an antigen, to which the subject has a known or suspected allergy, for oral ingestion. Methods of administering an oral food challenge may vary. For example, in some instances, a subject may be administered the antigen in an isolated, purified or enriched form, including but not limited to e.g., an extract or concentrate of a particular portion of the food allergen, such as e.g., peanut protein extract, peanut protein concentrate. In some instances, a subject may be administered the antigen in food form, e.g., in a whole, cooked, uncooked, or raw form, for ingestion by normal means. During an OFC a subject may or may not be administered other (i.e., non-antigen-containing) foodstuffs During a typical OFC, an OFC administrator (e.g., a healthcare professional, an allergist, a physician, a technician, nurse, etc.) may feed the suspected or known antigen, or food containing the suspected of known antigen, in one or more measured doses. The OFC administrator will generally begin with small amounts unlikely to trigger a symptomatic response in the subject. In some instances, with each dose, the OFC administrator or other healthcare professional will observe the subject for a period of time, evaluating the subject of one or more, including any, signs of a reaction. When no significant symptoms are observed, the challenge dose may be gradually increased and re-administered. In some instances, an OFC may be administered as a double-blind, placebo-controlled food challenge (DBPCFC), a single-blinded food challenge, or an open-food challenge.

Depending on the severity and the particular circumstances of the OFC, in some instances, when the subject displays one or more signs of a reaction the food challenge may be halted or terminated. Given the controlled nature of OFCs, observed reactions are generally mild, such as e.g., as flushing or hives, and severe reactions are uncommon. In instances where a subject displays a moderate and/or severe reaction, the subject may be administered one or more medications to relieve one or more symptoms if necessary or desired.

In some instances, antigen challenges are given to subjects not already known to have a food allergy. In some instances, antigen challenges are given to subjects already known to have a food allergy. Subject known to have a food allergy may be administered an antigen challenge for a variety of reasons including but not limited to e.g., to assess the severity of the food allergy condition of the subject, as part of a tolerance therapy, and the like.

Antigen challenges may be administered at any convenient point during a course of therapy including e.g., before, during, and/or after, administering a psychedelic agent to the subject according to the methods described herein. For example, in some instances, a subject may be administered an antigen challenge before being administered a psychedelic agent, including but not limited to e.g., as a means of assessing the subject for the food allergy and/or assessing the severity of a subject's food allergy condition. In some instances, a subject may be administered an antigen challenge during the administration of a psychedelic agent, including but not limited to e.g., as a means of causing the allergen and the psychedelic agent to be co-present in the subject's system. Correspondingly, depending on the half-life of the psychedelic agent, the allergen, or both, in some instances, an antigen challenge may be performed with such temporal proximity before or after administration of the psychedelic agent such that both of co-present in the subject's system. In some instances, a subject may be administered an antigen challenge after administration of the psychedelic agent, including but not limited to e.g., as a means of assessing the subject for the food allergy and/or assessing the severity of a subject's food allergy condition and/or assessing the effectiveness of the treatment.

In instances where an antigen challenge is employed, a subject method may include only one antigen challenge or multiple antigen challenges, including where each of the plurality of antigen challenges are administered at various points in the treatment schedule, including before, during, and/or after administration of one or more psychedelic agents. For example, where multiple antigen challenges are employed, in some instances, an antigen challenge may be performed before and/or during each administration of one or more psychedelic agents, including where the administered one or more psychedelic agents include the same agent or different agents.

In some instances, methods of the present disclosure may include one or more abstinent periods, e.g., as part of the treatment schedule. As used herein, an "abstinent period" generally refers to a period of time during which a subject abstains from one or more behaviors before, during and/or after administration of a psychedelic agent. The length of an abstinent period will vary depending e.g., on the purpose of the abstinent period. For example, where an abstinent period is prescribed in order to allow one or more substances to clear from a subject's body or blood stream, the length of an abstinent period may be based on the half-life of the substance(s). In some instances, an abstinent period may be at least 1 hour or more, including but not limited to e.g., at least 2 hours, at least 4 hours, at least 6 hours, at least 8 hours, at least 12 hours, at least 18 hours, at least 1 day, at least two days, at least 3 days, at least 4 days, at least 5 days, at least a week, at least two weeks, at least a month, etc.

One or more abstinent periods may be prescribed to be performed at any point in a subject method including, before, during and/or after administration of a psychedelic agent. In some instances, a subject method may include an abstinent period prior to administering one or more psychedelic agents. The substance(s) from which a subject may be required to abstain from during an abstinent period may vary and may e.g., include an antigen to which the subject is known to have an allergy, an antigen to which the subject may be suspected of having an allergy, one or more of over-the-counter medications, prescription medications, alcohol, illicit drugs and the like.

In some instances, an abstinent period may include requiring a subject to abstain from one or more mental health medications including but not limited to e.g., antidepressants (e.g., selective serotonin reuptake inhibitors (SSRIs), serotonin and norepinephrine reuptake inhibitors (SNRIs), tricyclics, tetracyclics, monoamine oxidase inhibitors (MAOIs), bupropion, etc.), anti-anxiety medications (e.g., benzodiazepines, etc.), stimulants (e.g., methylphenidate, amphetamine, dextroamphetamine, lisdexamfetamine dimesylate, etc.), antipsychotics (e.g., typical antipsychotics (i.e., neuroleptics), atypical antipsychotics, etc.), mood stabilizers (e.g., lithium, etc.), and the like.

In some instances, methods of the present disclosure may include or exclude the use of psychotherapy, e.g., depending on the specific treatment employed. In some instances, a subject method may include psychotherapy before, during and/or after the subject is administered the psychedelic agent. For example, in some instances, where a subject is administered a psychoactive dose of a psychedelic agent, psychotherapy may be performed during and/or after a psychedelic episode mediated by the agent. Where employed psychotherapy may be performed for various purposes, including but not limited to e.g., to guide a psychedelic experience of the subject, to integrate a psychedelic experience of the subject, and the like.

In some instances, psychotherapy may be performed prior to administering the subject a psychedelic agent. Psychotherapy may be formed before treatment with a psychedelic agent for various reasons including but not limited to e.g., to obtain a psychological evaluation of the subject prior to the administering. An obtained psychological evaluation may find various uses in the herein described methods including but not limited to e.g., determining whether to treat a subject using administration of a psychedelic agent, determining a starting dose for treating a subject with a psychedelic agent, evaluating the mental health state of a subject during and/or following treatment with a psychedelic agent, and the like.

Subjects

The methods described herein may be employed with a variety of different types of subjects, i.e., animals, where the animals are typically "mammals" or "mammalian," where these terms are used broadly to describe organisms which are within the class mammalia, including the orders carnivore (e.g., dogs and cats), rodentia (e.g., mice, guinea pigs, and rats), lagomorpha (e.g., rabbits) and primates (e.g., humans, chimpanzees, and monkeys). In many embodiments, the subjects or patients will be humans. In some instances, the subjects may be adult humans.

In some embodiments, the subject to which a psychedelic agent is administered has been diagnosed as having a food allergy condition. In some instances, the methods may include diagnosing the subject as having a food allergy condition. Diagnoses of such conditions may be made using any convenient protocol. In some instances, the subject is also one that has been determined to have a food allergy condition. As used herein, the term "food allergy condition" describes any overactivation or malfunction of the immune system in response to ingestion of a food substance.

Methods of the present disclosure may be employed for the treatment of food allergy syndrome. As used herein, the term "syndrome" refers to one or more symptoms that are characteristic of a specific disorder or disease. Thus, the phrase "food allergy syndrome" refers to one or more symptoms which are characteristic of or associated with a food allergy. As such, a food allergy syndrome condition is a condition associated with one or more symptoms characteristic of a food allergy. Accordingly, a food allergy syndrome condition is a condition that is related to reactions caused or exacerbated by a food allergy. Specific food allergy syndrome conditions that may be treated according to embodiments of the invention include, but are not limited to conditions having symptoms associated with the respiratory, digestive, integumentary, cardiovascular, and/or other body systems. In certain embodiments, food allergy syndrome conditions manifest as one or more symptoms, where such symptoms include, but are not limited to: bronchospasm, cough, rhinorrhea, angioedema, gastric hypermotility, urticaria, pruritis, fatigue, bradycardia, and/or hypotension. As the target condition of the methods described herein is a food allergy syndrome, the subject that is treated by methods of the invention is one that also has one or more food allergies with which the syndrome is associated.

The subject methods find use in the treatment of a variety of different food allergy syndrome conditions. Such food allergy syndrome conditions include, but are not limited to: conditions associated with the respiratory system including bronchospasm, cough, and rhinorrhea; conditions associated with the digestive system including gastric hypermotility; conditions associated with the integumentary system including angioedema, and urticaria, pruritis; conditions associated with the circulatory system including fatigue, bradycardia, and hypotension; and combinations thereof.

In some instances, methods of the invention may also result in treatment of symptoms of the food allergy for which the syndrome is associated. Such symptoms may vary, and may include: difficulty swallowing, hives, vomiting, shortness of breath, stomach cramps, runny nose, nausea, nasal congestion, lightheadedness, rash, diarrhea, fainting, abdominal pain, and swelling of the eyelids, face, lips, tongue or other areas, low blood pressure, blocked airways, and combinations thereof.

Food allergy conditions may, after exposure to an allergen, cause an anaphylactic condition in a subject. Accordingly, the methods of the present disclosure may, in some instances, treat, including prevent or lessen the severity of, anaphylaxis in a subject following exposure to an antigen. The term "anaphylaxis", as that term is used herein, refers to a broad class of immediate-type hypersensitivity and anaphylactic conditions well known to those skilled in the art including, but not limited to, anaphylactoid reactions, anaphylactic shock, idiopathic anaphylaxis, allergen induced anaphylaxis, exercise induced anaphylaxis, exercise-induced food-dependent anaphylaxis, active anaphylaxis, aggregate anaphylaxis, antiserum anaphylaxis, generalized anaphylaxis, inverse anaphylaxis, local anaphylaxis, passive anaphylaxis, reverse anaphylaxis, and systemic anaphylaxis. An "episode" of anaphylaxis, as the term is used herein, refers to a continuous manifestation of anaphylaxis in a patient.

Common food allergens to which a subject may be allergic include but are not limited to e.g., nuts and seeds (e.g., almond, brazil nut, cashew, chestnut, cocoa, coconut, cotton seed, flax seed, linseed, hazelnut, mustard, pecan, pine nut, poppy seed, sesame, sunflower seed (botanically a fruit), walnut, etc.); grains and cereals (e.g., barley, buckwheat, maize, oat, rice, rye, wheat, etc.); legumes (e.g., castor bean, chickpea, lentil, lupine, peanut, soybean, etc.), fruits (e.g., acerola, apple, apricot, avocado, banana, cherry, coconut, date, fig, garden plum, grape, kiwi fruit, lychee, mango, melon, peach, pear, persimmon, pineapple, pomegranate, strawberry, tomato, etc.); vegetables (e.g., cabbage, carrot, celery, zucchini, garlic, lettuce, potato, turnip, etc.); herbs and spices (e.g., aniseed, chamomile, celery, garlic, etc.); shellfish and snails (e.g., abalone, crab, lobster, oyster, shrimp, snail, squid, etc.); fish (e.g., Alaskan pollock, carp, cod, mackerel, salmon, tuna, etc.); chicken egg; bovine milk; and the like.

Psychedelic Agents

As summarized above, methods of the present disclosure include administering a psychedelic agent to a subject to treat the subject for a food allergy condition. The term "psychedelic agent", as used herein, generally refers to a class of psychoactive substances that produce profound alterations in perception, mood and/or numerous cognitive processes. Psychedelic agents include serotonergic hallucinogens that may, in some instances, bind and/or otherwise activate serotonin receptors, i.e., receptors for 5-hydroxytryptamine (5-HT). In some instances, psychedelic agents may act through activation of one or more 5-HT receptors, including e.g., a $5-HT_{1a}$ receptor, a $5-HT_{1b}$ receptor, a $5-HT_{1d}$ receptor, a $5-HT_{2a}$ receptor, a $5-HT_{2b}$ receptor, a $5-HT_{2c}$ receptor, etc. Psychedelic agents may be full or partial agonists of 5-HT receptors. In some instances, psychedelic agents employed may function through an atypical (i.e., non-5-HT) mechanism, including but not limited to e.g., opioid receptor agonism.

Various psychedelic agents may find use in the described methods, including but not necessarily limited to e.g., lysergamide psychedelic agents, tryptamine psychedelic agents, phenethylamine psychedelic agents, entactogen psychedelic agents, non-traditional psychedelic agents, and atypical psychedelic agents. Psychedelic agents of the will generally exclude active components of cannabis, including e.g., tetrahydrocannabinol (THC) and cannabinoids.

Lysergamides

Useful lysergamide psychedelic agents include but are not limited to e.g., 1-Propionyl-6-ethyl-6-nor-lysergic acid diethyamide (1P-ETH-LAD), 1-Propionyl-d-lysergic acid diethylamide (1P-LSD), 6-Allyl-6-nor-lysergic acid diethylamide (AL-LAD), 1-Acetyl-N,N-diethyllysergamide (ALD-52), 6-Ethyl-6-nor-lysergic acid diethylamide (ETH-LAD), d-lysergic acid amide (LSA), lysergic acid diethylamide (LSD), lysergic acid morpholide (LSM-775), lysergic acid 2,4-dimethylazetidide (LSZ), 6-Propynyl-6-nor-Lysergic acid diethylamide (PARGY-LAD), N-Propylnorlysergic acid N,N-diethylamide (PRO-LAD), and the like.

In some embodiments, 1P-ETH-LAD may be administered at or above a threshold dose, including but not limited to e.g., a threshold dose at or above 30 micrograms (ug), including e.g., where oral delivery is employed. In some instances, a threshold dose of 1P-ETH-LAD may range from 25 ug to 30 ug, including e.g., by oral delivery. In some embodiments, 1P-ETH-LAD may be administered as a light dose, including but not limited to e.g., a light dose ranging from 30 ug to 60 ug, including e.g., by oral delivery. In some embodiments, 1P-ETH-LAD may be administered as a common dose, including but not limited to e.g., a common dose ranging from 60 ug to 100 ug, including e.g., by oral delivery. In some embodiments, 1P-ETH-LAD may be administered as a strong dose, including but not limited to e.g., a strong dose ranging from 100 ug to 200 ug, including e.g., by oral delivery. In some embodiments, 1P-ETH-LAD may be administered as a heavy dose, including but not limited to e.g., where 1P-ETH-LAD is administered at a dose above 200 ug, e.g., by oral delivery.

In some embodiments, 1P-LSD may be administered at or above a threshold dose, including but not limited to e.g., a threshold dose at or above 15 micrograms (ug), including e.g., where oral delivery is employed. In some embodiments, 1P-LSD may be administered as a light dose, including but not limited to e.g., a light dose ranging from 25 ug to 75 ug, including e.g., by oral delivery. In some embodiments, 1P-LSD may be administered as a common dose, including but not limited to e.g., a common dose ranging from 75 ug to 150 ug, including e.g., by oral delivery. In some embodiments, 1P-LSD may be administered as a strong dose, including but not limited to e.g., a strong dose ranging from 150 ug to 300 ug, including e.g., by oral delivery. In some embodiments, 1P-LSD may be administered as a heavy dose, including but not limited to e.g., where 1P-LSD is administered at a dose above 300 ug, e.g., by oral delivery.

In some embodiments, AL-LAD may be administered at or above a threshold dose, including but not limited to e.g., a threshold dose at or above 50 micrograms (ug), including e.g., where oral delivery is employed. In some instances, a threshold dose of AL-LAD may range from 20 ug to 50 ug, including e.g., by oral delivery. In some embodiments, AL-LAD may be administered as a light dose, including but not limited to e.g., a light dose ranging from 50 ug to 100 ug, including e.g., by oral delivery. In some embodiments, AL-LAD may be administered as a common dose, including but not limited to e.g., a common dose ranging from 100 ug to 225 ug, including e.g., by oral delivery. In some embodiments, AL-LAD may be administered as a strong dose, including but not limited to e.g., a strong dose ranging from 225 ug to 350 ug, including e.g., by oral delivery. In some embodiments, AL-LAD may be administered as a heavy dose, including but not limited to e.g., where AL-LAD is administered at a dose above 350 ug, e.g., by oral delivery.

In some embodiments, ALD-52 may be administered at or above a threshold dose, including but not limited to e.g., a threshold dose at or above 30 micrograms (ug), including e.g., where oral delivery is employed. In some embodiments, ALD-52 may be administered as a light dose, including but not limited to e.g., a light dose ranging from 30 ug to 100 ug, including e.g., by oral delivery. In some embodiments, ALD-52 may be administered as a common dose, including but not limited to e.g., a common dose ranging from 100 ug to 175 ug, including e.g., by oral delivery. In some embodiments, ALD-52 may be administered as a strong dose, including but not limited to e.g., a strong dose ranging from 175 ug to 325 ug, including e.g., by oral delivery. In some embodiments, ALD-52 may be administered as a heavy dose, including but not limited to e.g., where ALD-52 is administered at a dose above 325 ug, e.g., by oral delivery.

In some embodiments, ETH-LAD may be administered at or above a threshold dose, including but not limited to e.g., a threshold dose at or above 30 micrograms (ug), including e.g., where oral delivery is employed. In some instances, a threshold dose of ETH-LAD may range from 15 ug to 30 ug, including e.g., by oral delivery. In some embodiments, ETH-LAD may be administered as a light dose, including but not limited to e.g., a light dose ranging from 30 ug to 60 ug, including e.g., by oral delivery. In some embodiments, ETH-LAD may be administered as a common dose, including but not limited to e.g., a common dose ranging from 60 ug to 150 ug, including e.g., by oral delivery. In some embodiments, ETH-LAD may be administered as a strong dose, including but not limited to e.g., a strong dose ranging from 150 ug to 225 ug, including e.g., by oral delivery. In some embodiments, ETH-LAD may be administered as a heavy dose, including but not limited to e.g., where ETH-LAD is administered at a dose above 225 ug, e.g., by oral delivery.

In some embodiments, LSA may be administered at or above a threshold dose, including but not limited to e.g., a threshold dose at or above 50 micrograms (ug), including e.g., where oral delivery is employed. In some instances, a threshold dose of LSA may range from 20 ug to 50 ug, including e.g., by oral delivery. In some embodiments, LSA may be administered as a light dose, including but not limited to e.g., a light dose ranging from 50 ug to 100 ug, including e.g., by oral delivery. In some embodiments, LSA may be administered as a common dose, including but not limited to e.g., a common dose ranging from 100 ug to 250 ug, including e.g., by oral delivery. In some embodiments, LSA may be administered as a strong dose, including but not limited to e.g., a strong dose ranging from 250 ug to 400 ug, including e.g., by oral delivery. In some embodiments, LSA may be administered as a heavy dose, including but not limited to e.g., where LSA is administered at a dose above 400 ug, e.g., by oral delivery.

In some embodiments, LSD may be administered at or above a threshold dose, including but not limited to e.g., a threshold dose at or above 25 micrograms (ug), including e.g., where oral delivery is employed. In some instances, a threshold dose of LSD may range from 15 ug to 25 ug, including e.g., by oral delivery. In some embodiments, LSD may be administered as a light dose, including but not limited to e.g., a light dose ranging from 25 ug to 75 ug, including e.g., by oral delivery. In some embodiments, LSD may be administered as a common dose, including but not limited to e.g., a common dose ranging from 75 ug to 150 ug, including e.g., by oral delivery. In some embodiments, LSD may be administered as a strong dose, including but not limited to e.g., a strong dose ranging from 150 ug to 300 ug, including e.g., by oral delivery. In some embodiments, LSD may be administered as a heavy dose, including but not limited to e.g., where LSD is administered at a dose above 300 ug, e.g., by oral delivery.

In some embodiments, LSM-775 may be administered at or above a threshold dose, including but not limited to e.g., a threshold dose at or above 500 micrograms (ug), including e.g., where oral delivery is employed. In some instances, a threshold dose of LSM-775 may range from 250 ug to 500 ug, including e.g., by oral delivery. In some embodiments, LSM-775 may be administered as a light dose, including but not limited to e.g., a light dose ranging from 500 ug to 750 ug, including e.g., by oral delivery. In some embodiments, LSM-775 may be administered as a common dose, including but not limited to e.g., a common dose ranging from 750 ug to 1250 ug, including e.g., by oral delivery. In some embodiments, LSM-775 may be administered as a strong dose, including but not limited to e.g., a strong dose ranging from 1250 ug to 1500 ug, including e.g., by oral delivery. In some embodiments, LSM-775 may be administered as a heavy dose, including but not limited to e.g., where LSM-775 is administered at a dose above 1500 ug, e.g., by oral delivery.

In some embodiments, LSZ may be administered at or above a threshold dose, including but not limited to e.g., a threshold dose at or above 100 micrograms (ug), including e.g., where oral delivery is employed. In some instances, a threshold dose of LSZ may range from 50 ug to 100 ug, including e.g., by oral delivery. In some embodiments, LSZ may be administered as a light dose, including but not limited to e.g., a light dose ranging from 100 ug to 150 ug, including e.g., by oral delivery. In some embodiments, LSZ may be administered as a common dose, including but not limited to e.g., a common dose ranging from 150 ug to 300 ug, including e.g., by oral delivery. In some embodiments, LSZ may be administered as a strong dose, including but not limited to e.g., a strong dose ranging from 300 ug to 400 ug, including e.g., by oral delivery. In some embodiments, LSZ may be administered as a heavy dose, including but not limited to e.g., where LSZ is administered at a dose above 400 ug, e.g., by oral delivery.

In some embodiments, PARGY-LAD may be administered at or above a threshold dose, including but not limited to e.g., a threshold dose at or above 125 micrograms (ug), including e.g., where oral delivery is employed. In some instances, a threshold dose of PARGY-LAD may range from 50 ug to 125 ug, including e.g., by oral delivery. In some embodiments, PARGY-LAD may be administered as a light dose, including but not limited to e.g., a light dose ranging from 125 ug to 275 ug, including e.g., by oral delivery. In some embodiments, PARGY-LAD may be administered as a common dose, including but not limited to e.g., a common dose ranging from 275 ug to 500 ug, including e.g., by oral delivery. In some embodiments, PARGY-LAD may be administered as a strong dose, including but not limited to e.g., a strong dose ranging from 500 ug to 700 ug, including e.g., by oral delivery. In some embodiments, PARGY-LAD may be administered as a heavy dose, including but not limited to e.g., where PARGY-LAD is administered at a dose above 700 ug, e.g., by oral delivery.

In some embodiments, PRO-LAD may be administered at or above a threshold dose, including but not limited to e.g., a threshold dose at or above 50 micrograms (ug), including e.g., where oral delivery is employed. In some instances, a threshold dose of PRO-LAD may range from 20 ug to 50 ug, including e.g., by oral delivery. In some embodiments, PRO-LAD may be administered as a light dose, including but not limited to e.g., a light dose ranging from 50 ug to 100 ug, including e.g., by oral delivery. In some embodiments, PRO-LAD may be administered as a common dose, including but not limited to e.g., a common dose ranging from 100 ug to 200 ug, including e.g., by oral delivery. In some embodiments, PRO-LAD may be administered as a strong dose, including but not limited to e.g., a strong dose ranging from 200 ug to 400 ug, including e.g., by oral delivery. In some embodiments, PRO-LAD may be administered as a heavy dose, including but not limited to e.g., where PRO-LAD is administered at a dose above 400 ug, e.g., by oral delivery.

Tryptamines

Useful tryptamine psychedelic agents include but are not limited to e.g., diethyltryptamine (DET), N,N-dimethyltryptamine (DMT), N,N-Dipropyltryptamine (DPT), N,N-Dipropyltryptamine (DPT), N,N-Diisopropyltryptamine (DiPT), N,N-Diisopropyltryptamine (DiPT), N-Ethyl-N-propyltryptamine (EPT), N-Ethyl-N-methyltryptamine (MET), N-Ethyl-N-methyltryptamine (MET), N-Ethyl-N-methyltryptamine (MET), N-Methyl-N-isopropyltryptamine (MiPT), α-Methyltryptamine (aMT), 4-Acetoxy-N,N-diethyltryptamine (4-AcO-DET), 4-Acetoxy-N,N-dimethyltryptamine (4-AcO-DMT), 4-Acetoxy-N,N-dimethyltryptamine (4-AcO-DMT), 4-Acetoxy-N,N-diisopropyltryptamine (4-AcO-Di PT), 4-Acetoxy-N-ethyl-N-methyltryptamine (4-AcO-MET), 4-Acetoxy-N-methyl-N-isopropyltryptamine (4-AcO-MiPT), 4-Hydroxy-N,N-diethyltryptamine (4-HO-DET), 4-Hydroxy-N,N-dimethyltryptamine (4-HO-DMT), 4-hydroxy-dipropyltryptamine (4-HO-DPT), 4-Hydroxy-diisopropyltryptamine (4-HO-DiPT), 4-Hydroxy-N-ethyl-N-propyltryptamine (4-HO-EPT), 4-Hydroxy-N-methyl-N-ethyltryptamine (4-HO-MET), 4-Hydroxy-N-methyl-N-ethyltryptamine (4-HO-MET), 4-Hydroxy-N-methyl-N-propyltryptamine (4-HO-MPT), 4-Hydroxy-N-methyl-N-isopropyltryptamine (4-HO-MiPT), 5-Hydroxy-N,N-dimethyltryptamine (5-HO-DMT), N,N-Diallyl-5-methoxytryptamine (5-MeO-DALT), N,N-Diallyl-5-methoxytryptamine (5-MeO-DALT), 5-Methoxy-N,N-dimethyltryptamine (5-MeO-DMT), 5-Methoxy-N,N-diisopropyltryptamine (5-MeO-DiPT), 5-Methoxy-N-methyl-N-isopropyltryptamine (5-MeO-MiPT), 5-Methoxy-N-methyl-N-isopropyltryptamine (5-MeO-MiPT), 12-Methoxyibogamine (10-Methoxyibogamine) (Ibogaine), and the like.

In some embodiments, DET may be administered at or above a threshold dose, including but not limited to e.g., a threshold dose at or above 20 milligrams (mg), including e.g., where oral delivery is employed. In some instances, a threshold dose of DET may range from 10 mg to 20 mg, including e.g., by oral delivery. In some embodiments, DET may be administered as a light dose, including but not limited to e.g., a light dose ranging from 20 mg to 40 mg, including e.g., by oral delivery. In some embodiments, DET may be administered as a common dose, including but not limited to e.g., a common dose ranging from 40 mg to 70 mg, including e.g., by oral delivery. In some embodiments, DET may be administered as a strong dose, including but not limited to e.g., a strong dose ranging from 70 mg to 100 mg, including e.g., by oral delivery. In some embodiments, DET may be administered as a heavy dose, including but not limited to e.g., where DET is administered at a dose above 100 mg, e.g., by oral delivery.

In some embodiments, DMT may be administered at or above a threshold dose, including but not limited to e.g., a threshold dose at or above 10 milligrams (mg), including e.g., where smoked delivery is employed. In some instances, a threshold dose of DMT may range from 2 mg to 10 mg, including e.g., by smoked delivery. In some embodiments, DMT may be administered as a light dose, including but not limited to e.g., a light dose ranging from 10 mg to 20 mg, including e.g., by smoked delivery. In some embodiments, DMT may be administered as a common dose, including but not limited to e.g., a common dose ranging from 20 mg to 40 mg, including e.g., by smoked delivery. In some embodiments, DMT may be administered as a strong dose, including but not limited to e.g., a strong dose ranging from 40 mg to 60 mg, including e.g., by smoked delivery. In some embodiments, DMT may be administered as a heavy dose, including but not limited to e.g., where DMT is administered at a dose above 60 mg, e.g., by smoked delivery.

In some embodiments, DPT may be administered at or above a threshold dose, including but not limited to e.g., a threshold dose at or above 15 milligrams (mg), including e.g., where smoked delivery is employed. In some instances, a threshold dose of DPT may range from 10 mg to 15 mg, including e.g., by smoked delivery. In some embodiments, DPT may be administered as a light dose, including but not limited to e.g., a light dose ranging from 15 mg to 20 mg, including e.g., by smoked delivery. In some embodiments, DPT may be administered as a common dose, including but not limited to e.g., a common dose ranging from 20 mg to 50 mg, including e.g., by smoked delivery. In some embodiments, DPT may be administered as a strong dose, including but not limited to e.g., a strong dose ranging from 50 mg to 100 mg, including e.g., by smoked delivery. In some embodiments, DPT may be administered as a heavy dose, including but not limited to e.g., where DPT is administered at a dose above 100 mg, e.g., by smoked delivery.

In some embodiments, DPT may be administered at or above a threshold dose, including but not limited to e.g., a threshold dose at or above 75 milligrams (mg), including e.g., where oral delivery is employed. In some instances, a threshold dose of DPT may range from 50 mg to 75 mg, including e.g., by oral delivery. In some embodiments, DPT may be administered as a light dose, including but not limited to e.g., a light dose ranging from 75 mg to 150 mg, including e.g., by oral delivery. In some embodiments, DPT may be administered as a common dose, including but not limited to e.g., a common dose ranging from 150 mg to 250 mg, including e.g., by oral delivery. In some embodiments, DPT may be administered as a strong dose, including but not limited to e.g., a strong dose ranging from 250 mg to 250 mg, including e.g., by oral delivery. In some embodiments, DPT may be administered as a heavy dose, including but not limited to e.g., where DPT is administered at a dose above 350 mg, e.g., by oral delivery.

In some embodiments, DiPT may be administered at or above a threshold dose, including but not limited to e.g., a threshold dose at or above 10 milligrams (mg), including e.g., where smoked delivery is employed. In some instances, a threshold dose of DiPT may range from 5 mg to 10 mg, including e.g., by smoked delivery. In some embodiments, DiPT may be administered as a light dose, including but not limited to e.g., a light dose ranging from 10 mg to 15 mg, including e.g., by smoked delivery. In some embodiments, DiPT may be administered as a common dose, including but not limited to e.g., a common dose ranging from 15 mg to 20 mg, including e.g., by smoked delivery. In some embodiments, DiPT may be administered as a strong dose, including but not limited to e.g., a strong dose ranging from 20 mg to 30 mg, including e.g., by smoked delivery. In some embodiments, DiPT may be administered as a heavy dose, including but not limited to e.g., where DiPT is administered at a dose above 30 mg, e.g., by smoked delivery.

In some embodiments, DiPT may be administered at or above a threshold dose, including but not limited to e.g., a threshold dose at or above 15 milligrams (mg), including e.g., where oral delivery is employed. In some embodiments, DiPT may be administered as a light dose, including but not limited to e.g., a light dose ranging from 15 mg to 30 mg, including e.g., by oral delivery. In some embodiments, DiPT may be administered as a common dose, including but not limited to e.g., a common dose ranging from 30 mg to 75 mg, including e.g., by oral delivery. In some embodiments, DiPT may be administered as a strong dose, including but not limited to e.g., a strong dose ranging from 75 mg to 150 mg, including e.g., by oral delivery. In some embodiments, DiPT may be administered as a heavy dose, including but not limited to e.g., where DiPT is administered at a dose above 150 mg, e.g., by oral delivery.

In some embodiments, EPT may be administered at or above a threshold dose, including but not limited to e.g., a threshold dose at or above 20 milligrams (mg), including e.g., where insufflated delivery is employed. In some embodiments, EPT may be administered as a light dose, including but not limited to e.g., a light dose ranging from 20 mg to 40 mg, including e.g., by insufflated delivery. In some embodiments, EPT may be administered as a common dose, including but not limited to e.g., a common dose ranging from 40 mg to 80 mg, including e.g., by insufflated delivery. In some embodiments, EPT may be administered as a strong dose, including but not limited to e.g., a strong dose ranging from 80 mg to 110 mg, including e.g., by insufflated delivery. In some embodiments, EPT may be administered as a heavy dose, including but not limited to e.g., where EPT is administered at a dose above 110 mg, e.g., by insufflated delivery.

In some embodiments, MET may be administered at or above a threshold dose, including but not limited to e.g., a threshold dose at or above 20 milligrams (mg), including e.g., where smoked delivery is employed. In some instances, a threshold dose of MET may range from 10 mg to 20 mg, including e.g., by smoked delivery. In some embodiments, MET may be administered as a light dose, including but not limited to e.g., a light dose ranging from 20 mg to 40 mg, including e.g., by smoked delivery. In some embodiments, MET may be administered as a common dose, including but not limited to e.g., a common dose ranging from 40 mg to 60 mg, including e.g., by smoked delivery. In some embodiments, MET may be administered as a strong dose, including but not limited to e.g., a strong dose ranging from 60 mg to 90 mg, including e.g., by smoked delivery. In some embodiments, MET may be administered as a heavy dose, including but not limited to e.g., where MET is administered at a dose above 90 mg, e.g., by smoked delivery.

In some embodiments, MET may be administered at or above a threshold dose, including but not limited to e.g., a threshold dose at or above 60 milligrams (mg), including e.g., where oral delivery is employed. In some instances, a threshold dose of MET may range from 40 mg to 60 mg, including e.g., by oral delivery. In some embodiments, MET may be administered as a light dose, including but not limited to e.g., a light dose ranging from 60 mg to 120 mg, including e.g., by oral delivery. In some embodiments, MET may be administered as a common dose, including but not limited to e.g., a common dose ranging from 120 mg to 150 mg, including e.g., by oral delivery. In some embodiments, MET may be administered as a strong dose, including but not limited to e.g., a strong dose ranging from 150 mg to 200 mg, including e.g., by oral delivery. In some embodiments, MET may be administered as a heavy dose, including but not limited to e.g., where MET is administered at a dose above 200 mg, e.g., by oral delivery.

In some embodiments, MET may be administered at or above a threshold dose, including but not limited to e.g., a threshold dose at or above 10 milligrams (mg), including e.g., where insufflated delivery is employed. In some instances, a threshold dose of MET may range from 5 mg to 10 mg, including e.g., by insufflated delivery. In some embodiments, MET may be administered as a light dose, including but not limited to e.g., a light dose ranging from 10 mg to 20 mg, including e.g., by insufflated delivery. In some embodiments, MET may be administered as a common dose, including but not limited to e.g., a common dose ranging from 20 mg to 25 mg, including e.g., by insufflated delivery. In some embodiments, MET may be administered as a strong dose, including but not limited to e.g., a strong dose ranging from 25 mg to 35 mg, including e.g., by insufflated delivery. In some embodiments, MET may be administered as a heavy dose, including but not limited to e.g., where MET is administered at a dose above 35 mg, e.g., by insufflated delivery.

In some embodiments, MiPT may be administered as a common dose, including but not limited to e.g., a common dose ranging from 10 mg to 25 mg, including e.g., by oral delivery.

In some embodiments, aMT (aka indopan) may be administered at or above a threshold dose, including but not limited to e.g., a threshold dose at or above 10 milligrams (mg), including e.g., where oral delivery is employed. In some instances, a threshold dose of aMT may range from 5 mg to 10 mg, including e.g., by oral delivery. In some embodiments, aMT may be administered as a light dose, including but not limited to e.g., a light dose ranging from 10 mg to 25 mg, including e.g., by oral delivery. In some embodiments, aMT may be administered as a common dose, including but not limited to e.g., a common dose ranging from 25 mg to 40 mg, including e.g., by oral delivery. In some embodiments, aMT may be administered as a strong dose, including but not limited to e.g., a strong dose ranging from 40 mg to 60 mg, including e.g., by oral delivery. In some embodiments, aMT may be administered as a heavy dose, including but not limited to e.g., where aMT is administered at a dose above 60 mg, e.g., by oral delivery.

In some embodiments, 4-AcO-DET (aka ethacetin) may be administered at or above a threshold dose, including but not limited to e.g., a threshold dose at or above 10 milligrams (mg), including e.g., where oral delivery is employed. In some instances, a threshold dose of 4-AcO-DET may range from 5 mg to 10 mg, including e.g., by oral delivery. In some embodiments, 4-AcO-DET may be administered as a light dose, including but not limited to e.g., a light dose ranging from 10 mg to 15 mg, including e.g., by oral delivery. In some embodiments, 4-AcO-DET may be administered as a common dose, including but not limited to e.g., a common dose ranging from 15 mg to 20 mg, including e.g., by oral delivery. In some embodiments, 4-AcO-DET may be administered as a strong dose, including but not limited to e.g., a strong dose ranging from 20 mg to 35 mg, including e.g., by oral delivery. In some embodiments, 4-AcO-DET may be administered as a heavy dose, including but not limited to e.g., where 4-AcO-DET is administered at a dose above 35 mg, e.g., by oral delivery.

In some embodiments, 4-AcO-DMT (aka psilacetin) may be administered at or above a threshold dose, including but not limited to e.g., a threshold dose at or above 7.5 milligrams (mg), including e.g., where oral delivery is employed. In some instances, a threshold dose of 4-AcO-DMT may range from 5 mg to 7.5 mg, including e.g., by oral delivery. In some embodiments, 4-AcO-DMT may be administered as a light dose, including but not limited to e.g., a light dose ranging from 7.5 mg to 15 mg, including e.g., by oral delivery. In some embodiments, 4-AcO-DMT may be administered as a common dose, including but not limited to e.g., a common dose ranging from 15 mg to 25 mg, including e.g., by oral delivery. In some embodiments, 4-AcO-DMT may be administered as a strong dose, including but not limited to e.g., a strong dose ranging from 25 mg to 45 mg, including e.g., by oral delivery. In some embodiments, 4-AcO-DMT may be administered as a heavy dose, including but not limited to e.g., where 4-AcO-DMT is administered at a dose above 45 mg, e.g., by oral delivery.

In some embodiments, 4-AcO-DMT (aka psilacetin) may be administered at or above a threshold dose, including but not limited to e.g., a threshold dose at or above 10 milligrams (mg), including e.g., where insufflated delivery is employed. In some instances, a threshold dose of 4-AcO-DMT may range from 5 mg to 10 mg, including e.g., by insufflated delivery. In some embodiments, 4-AcO-DMT may be administered as a light dose, including but not limited to e.g., a light dose ranging from 10 mg to 15 mg, including e.g., by insufflated delivery. In some embodiments, 4-AcO-DMT may be administered as a common dose, including but not limited to e.g., a common dose ranging from 15 mg to 25 mg, including e.g., by insufflated delivery. In some embodiments, 4-AcO-DMT may be administered as a strong dose, including but not limited to e.g., a strong dose ranging from 25 mg to 20 mg, including e.g., by insufflated delivery. In some embodiments, 4-AcO-DMT may be administered as a heavy dose, including but not limited to e.g., where 4-AcO-DMT is administered at a dose above 50 mg, e.g., by insufflated delivery.

In some embodiments, 4-AcO-DiPT (aka ipracetin) may be administered at or above a threshold dose, including but not limited to e.g., a threshold dose at or above 5 milligrams (mg), including e.g., where oral delivery is employed. In some instances, a threshold dose of 4-AcO-DiPT may range from 3 mg to 5 mg, including e.g., by oral delivery. In some embodiments, 4-AcO-DiPT may be administered as a light dose, including but not limited to e.g., a light dose ranging from 5 mg to 15 mg, including e.g., by oral delivery. In some embodiments, 4-AcO-DiPT may be administered as a common dose, including but not limited to e.g., a common dose ranging from 15 mg to 30 mg, including e.g., by oral delivery. In some embodiments, 4-AcO-DiPT may be administered as a strong dose, including but not limited to e.g., a strong dose ranging from 30 mg to 45 mg, including e.g., by oral delivery. In some embodiments, 4-AcO-DiPT may be administered as a heavy dose, including but not limited to e.g., where 4-AcO-DiPT is administered at a dose above 45 mg, e.g., by oral delivery.

In some embodiments, 4-AcO-MET (aka metacetin) may be administered at or above a threshold dose, including but not limited to e.g., a threshold dose at or above 10 milligrams (mg), including e.g., where oral delivery is employed. In some instances, a threshold dose of 4-AcO-MET may range from 5 mg to 10 mg, including e.g., by oral delivery. In some embodiments, 4-AcO-MET may be administered as a light dose, including but not limited to e.g., a light dose ranging from 10 mg to 20 mg, including e.g., by oral delivery. In some embodiments, 4-AcO-MET may be administered as a common dose, including but not limited to e.g., a common dose ranging from 20 mg to 30 mg, including e.g., by oral delivery. In some embodiments, 4-AcO-MET may be administered as a strong dose, including but not limited to e.g., a strong dose ranging from 30 mg to 50 mg, including e.g., by oral delivery. In some embodiments, 4-AcO-MET may be administered as a heavy dose, including but not limited to e.g., where 4-AcO-MET is administered at a dose above 50 mg, e.g., by oral delivery.

In some embodiments, 4-AcO-MiPT (aka mipracetin) may be administered at or above a threshold dose, including but not limited to e.g., a threshold dose at or above 10 milligrams (mg), including e.g., where oral delivery is employed. In some instances, a threshold dose of 4-AcO-MiPT may range from 5 mg to 10 mg, including e.g., by oral delivery. In some embodiments, 4-AcO-MiPT may be administered as a light dose, including but not limited to e.g., a light dose ranging from 10 mg to 15 mg, including e.g., by oral delivery. In some embodiments, 4-AcO-MiPT may be administered as a common dose, including but not limited to e.g., a common dose ranging from 15 mg to 20 mg, including e.g., by oral delivery. In some embodiments, 4-AcO-MiPT may be administered as a strong dose, including but not limited to e.g., a strong dose ranging from 20 mg to 35 mg, including e.g., by oral delivery. In some embodiments, 4-AcO-MiPT may be administered as a heavy dose, including but not limited to e.g., where 4-AcO-MiPT is administered at a dose above 35 mg, e.g., by oral delivery.

In some embodiments, 4-HO-DET (aka ethocin) may be administered at or above a threshold dose, including but not limited to e.g., a threshold dose at or above 10 milligrams (mg), including e.g., where oral delivery is employed. In some instances, a threshold dose of 4-HO-DET may range from 5 mg to 10 mg, including e.g., by oral delivery. In some embodiments, 4-HO-DET may be administered as a light dose, including but not limited to e.g., a light dose ranging from 10 mg to 15 mg, including e.g., by oral delivery. In some embodiments, 4-HO-DET may be administered as a common dose, including but not limited to e.g., a common dose ranging from 20 mg to 30 mg, including e.g., by oral delivery. In some embodiments, 4-HO-DET may be administered as a strong dose, including but not limited to e.g., a strong dose ranging from 30 mg to 45 mg, including e.g., by oral delivery. In some embodiments, 4-HO-DET may be administered as a heavy dose, including but not limited to e.g., where 4-HO-DET is administered at a dose above 45 mg, e.g., by oral delivery.

In some embodiments, 4-HO-DMT (aka psilocin) may be administered at or above a threshold dose, including but not limited to e.g., a threshold dose at or above 10 milligrams (mg), including e.g., where oral delivery is employed. In some instances, a threshold dose of 4-HO-DMT may range from 5 mg to 10 mg, including e.g., by oral delivery. In some embodiments, 4-HO-DMT may be administered as a light dose, including but not limited to e.g., a light dose ranging from 10 mg to 15 mg, including e.g., by oral delivery. In some embodiments, 4-HO-DMT may be administered as a common dose, including but not limited to e.g., a common dose ranging from 15 mg to 25 mg, including e.g., by oral delivery. In some embodiments, 4-HO-DMT may be administered as a strong dose, including but not limited to e.g., a strong dose ranging from 25 mg to 40 mg, including e.g., by oral delivery. In some embodiments, 4-HO-DMT may be administered as a heavy dose, including but not limited to e.g., where 4-HO-DMT is administered at a dose above 40 mg, e.g., by oral delivery.

In some embodiments, 4-HO-DPT (aka procin) may be administered at or above a threshold dose, including but not limited to e.g., a threshold dose at or above 40 milligrams (mg), including e.g., where oral delivery is employed. In some instances, a threshold dose of 4-HO-DPT may range from 20 mg to 40 mg, including e.g., by oral delivery. In some embodiments, 4-HO-DPT may be administered as a light dose, including but not limited to e.g., a light dose ranging from 40 mg to 60 mg, including e.g., by oral delivery. In some embodiments, 4-HO-DPT may be administered as a common dose, including but not limited to e.g., a common dose ranging from 60 mg to 90 mg, including e.g., by oral delivery. In some embodiments, 4-HO-DPT may be administered as a strong dose, including but not limited to e.g., a strong dose ranging from 90 mg to 130 mg, including e.g., by oral delivery. In some embodiments, 4-HO-DPT may be administered as a heavy dose, including but not limited to e.g., where 4-HO-DPT is administered at a dose above 130 mg, e.g., by oral delivery.

In some embodiments, 4-HO-DiPT (aka iprocin) may be administered at or above a threshold dose, including but not limited to e.g., a threshold dose at or above 3 milligrams (mg), including e.g., where oral delivery is employed. In some embodiments, 4-HO-DiPT may be administered as a light dose, including but not limited to e.g., a light dose ranging from 3 mg to 10 mg, including e.g., by oral delivery. In some embodiments, 4-HO-DiPT may be administered as a common dose, including but not limited to e.g., a common dose ranging from 10 mg to 20 mg, including e.g., by oral delivery. In some embodiments, 4-HO-DiPT may be administered as a strong dose, including but not limited to e.g., a strong dose ranging from 20 mg to 30 mg, including e.g., by oral delivery. In some embodiments, 4-HO-DiPT may be administered as a heavy dose, including but not limited to e.g., where 4-HO-DiPT is administered at a dose above 30 mg, e.g., by oral delivery.

In some embodiments, 4-HO-EPT (aka eprocin) may be administered as a common dose, including but not limited to e.g., a common dose ranging from 25 mg to 50 mg, including e.g., by oral delivery.

In some embodiments, 4-HO-MET (aka metocin) may be administered at or above a threshold dose, including but not limited to e.g., a threshold dose at or above 10 milligrams (mg), including e.g., where smoked delivery is employed. In some instances, a threshold dose of 4-HO-MET may range from 5 mg to 10 mg, including e.g., by smoked delivery. In some embodiments, 4-HO-MET may be administered as a light dose, including but not limited to e.g., a light dose ranging from 10 mg to 25 mg, including e.g., by smoked delivery. In some embodiments, 4-HO-MET may be administered as a common dose, including but not limited to e.g., a common dose ranging from 25 mg to 35 mg, including e.g., by smoked delivery. In some embodiments, 4-HO-MET may be administered as a strong dose, including but not limited to e.g., a strong dose ranging from 35 mg to 60 mg, including e.g., by smoked delivery. In some embodiments, 4-HO-MET may be administered as a heavy dose, including but not limited to e.g., where 4-HO-MET is administered at a dose above 60 mg, e.g., by smoked delivery.

In some embodiments, 4-HO-MET (aka metocin) may be administered at or above a threshold dose, including but not limited to e.g., a threshold dose at or above 5 milligrams (mg), including e.g., where oral delivery is employed. In some embodiments, 4-HO-MET may be administered as a light dose, including but not limited to e.g., a light dose ranging from 5 mg to 15 mg, including e.g., by oral delivery. In some embodiments, 4-HO-MET may be administered as a common dose, including but not limited to e.g., a common dose ranging from 15 mg to 25 mg, including e.g., by oral delivery. In some embodiments, 4-HO-MET may be administered as a strong dose, including but not limited to e.g., a strong dose ranging from 25 mg to 45 mg, including e.g., by oral delivery. In some embodiments, 4-HO-MET may be administered as a heavy dose, including but not limited to e.g., where 4-HO-MET is administered at a dose above 45 mg, e.g., by oral delivery.

In some embodiments, 4-HO-MPT (aka meprocin) may be administered at or above a threshold dose, including but not limited to e.g., a threshold dose at or above 10 milligrams (mg), including e.g., where oral delivery is employed. In some instances, a threshold dose of 4-HO-MPT may range from 5 mg to 10 mg, including e.g., by oral delivery. In some embodiments, 4-HO-MPT may be administered as a light dose, including but not limited to e.g., a light dose ranging from 10 mg to 20 mg, including e.g., by oral delivery. In some embodiments, 4-HO-MPT may be administered as a common dose, including but not limited to e.g., a common dose ranging from 20 mg to 30 mg, including e.g., by oral delivery. In some embodiments, 4-HO-MPT may be administered as a strong dose, including but not limited to e.g., a strong dose ranging from 30 mg to 50 mg, including e.g., by oral delivery. In some embodiments, 4-HO-MPT may be administered as a heavy dose, including but not limited to e.g., where 4-HO-MPT is administered at a dose above 50 mg, e.g., by oral delivery.

In some embodiments, 4-HO-MiPT (aka miprocin) may be administered at or above a threshold dose, including but not limited to e.g., a threshold dose at or above 10 milligrams (mg), including e.g., where oral delivery is employed. In some instances, a threshold dose of 4-HO-MiPT may range from 5 mg to 10 mg, including e.g., by oral delivery. In some embodiments, 4-HO-MiPT may be administered as a light dose, including but not limited to e.g., a light dose ranging from 10 mg to 15 mg, including e.g., by oral delivery. In some embodiments, 4-HO-MiPT may be administered as a common dose, including but not limited to e.g., a common dose ranging from 15 mg to 25 mg, including e.g., by oral delivery. In some embodiments, 4-HO-MiPT may be administered as a strong dose, including but not limited to e.g., a strong dose ranging from 25 mg to 35 mg, including e.g., by oral delivery. In some embodiments, 4-HO-MiPT may be administered as a heavy dose, including but not limited to e.g., where 4-HO-MiPT is administered at a dose above 35 mg, e.g., by oral delivery.

In some embodiments, 5-HO-DMT (aka bufotenin) may be administered at or above a threshold dose, including but not limited to e.g., a threshold dose at or above 5 milligrams (mg), including e.g., where smoked delivery is employed. In some instances, a threshold dose of 5-HO-DMT may range from 2 mg to 5 mg, including e.g., by smoked delivery. In some embodiments, 5-HO-DMT may be administered as a light dose, including but not limited to e.g., a light dose ranging from 5 mg to 20 mg, including e.g., by smoked delivery. In some embodiments, 5-HO-DMT may be administered as a common dose, including but not limited to e.g., a common dose ranging from 20 mg to 40 mg, including e.g., by smoked delivery. In some embodiments, 5-HO-DMT may be administered as a strong dose, including but not limited to e.g., a strong dose ranging from 40 mg to 60 mg, including e.g., by smoked delivery. In some embodiments, 5-HO-DMT may be administered as a heavy dose, including but not limited to e.g., where 5-HO-DMT is administered at a dose above 60 mg, e.g., by smoked delivery.

In some embodiments, 5-MeO-DALT (aka foxtrot) may be administered at or above a threshold dose, including but not limited to e.g., a threshold dose at or above 3 milligrams (mg), including e.g., where smoked delivery is employed. In some embodiments, 5-MeO-DALT may be administered as a common dose, including but not limited to e.g., a common dose ranging from 5 mg to 10 mg, including e.g., by smoked delivery.

In some embodiments, 5-MeO-DALT (aka foxtrot) may be administered at or above a threshold dose, including but not limited to e.g., a threshold dose at or above 5 milligrams (mg), including e.g., where oral delivery is employed. In some instances, a threshold dose of 5-MeO-DALT may range from 4 mg to 5 mg, including e.g., by oral delivery. In some embodiments, 5-MeO-DALT may be administered as a light dose, including but not limited to e.g., a light dose ranging from 5 mg to 12 mg, including e.g., by oral delivery. In some embodiments, 5-MeO-DALT may be administered as a common dose, including but not limited to e.g., a common dose ranging from 12 mg to 25 mg, including e.g., by oral delivery. In some embodiments, 5-MeO-DALT may be administered as a strong dose, including but not limited to e.g., a strong dose ranging from 25 mg to 35 mg, including e.g., by oral delivery. In some embodiments, 5-MeO-DALT may be administered as a heavy dose, including but not limited to e.g., where 5-MeO-DALT is administered at a dose above 35 mg, e.g., by oral delivery.

In some embodiments, 5-MeO-DMT (aka toad) may be administered at or above a threshold dose, including but not limited to e.g., a threshold dose at or above 3 milligrams (mg), including e.g., where smoked delivery is employed. In some instances, a threshold dose of 5-MeO-DMT may range from 1 mg to 3 mg, including e.g., by smoked delivery. In some embodiments, 5-MeO-DMT may be administered as a light dose, including but not limited to e.g., a light dose ranging from 3 mg to 6 mg, including e.g., by smoked delivery. In some embodiments, 5-MeO-DMT may be administered as a common dose, including but not limited to e.g., a common dose ranging from 6 mg to 12 mg, including e.g., by smoked delivery. In some embodiments, 5-MeO-DMT may be administered as a strong dose, including but not limited to e.g., a strong dose ranging from 12 mg to 20 mg, including e.g., by smoked delivery. In some embodiments, 5-MeO-DMT may be administered as a heavy dose, including but not limited to e.g., where 5-MeO-DMT is administered at a dose above 20 mg, e.g., by smoked delivery.

In some embodiments, 5-MeO-DiPT (aka foxy) may be administered at or above a threshold dose, including but not limited to e.g., a threshold dose at or above 3 milligrams (mg), including e.g., where oral delivery is employed. In some embodiments, 5-MeO-Di PT may be administered as a light dose, including but not limited to e.g., a light dose ranging from 3 mg to 10 mg, including e.g., by oral delivery. In some embodiments, 5-MeO-Di PT may be administered as a common dose, including but not limited to e.g., a common dose ranging from 10 mg to 15 mg, including e.g., by oral delivery. In some embodiments, 5-MeO-DiPT may be administered as a strong dose, including but not limited to e.g., a strong dose ranging from 15 mg to 20 mg, including e.g., by oral delivery. In some embodiments, 5-MeO-Di PT may be administered as a heavy dose, including but not limited to e.g., where 5-MeO-DiPT is administered at a dose above 20 mg, e.g., by oral delivery.

In some embodiments, 5-MeO-MiPT (aka moxy) may be administered at or above a threshold dose, including but not limited to e.g., a threshold dose at or above 5 milligrams (mg), including e.g., where smoked delivery is employed. In some embodiments, 5-MeO-MiPT may be administered as a light dose, including but not limited to e.g., a light dose ranging from 5 mg to 10 mg, including e.g., by smoked delivery. In some embodiments, 5-MeO-MiPT may be administered as a common dose, including but not limited to e.g., a common dose ranging from 10 mg to 15 mg, including e.g., by smoked delivery. In some embodiments, 5-MeO-MiPT may be administered as a strong dose, including but not limited to e.g., a strong dose ranging from 15 mg to 20 mg, including e.g., by smoked delivery. In some embodiments, 5-MeO-MiPT may be administered as a heavy dose, including but not limited to e.g., where 5-MeO-MiPT is administered at a dose above 20 mg, e.g., by smoked delivery.

In some embodiments, 5-MeO-MiPT (aka moxy) may be administered at or above a threshold dose, including but not limited to e.g., a threshold dose at or above 3 milligrams (mg), including e.g., where oral delivery is employed. In some embodiments, 5-MeO-MiPT may be administered as a light dose, including but not limited to e.g., a light dose ranging from 3 mg to 7 mg, including e.g., by oral delivery. In some embodiments, 5-MeO-MiPT may be administered as a common dose, including but not limited to e.g., a common dose ranging from 7 mg to 15 mg, including e.g., by oral delivery. In some embodiments, 5-MeO-MiPT may be administered as a strong dose, including but not limited to e.g., a strong dose ranging from 15 mg to 20 mg, including e.g., by oral delivery. In some embodiments, 5-MeO-MiPT may be administered as a heavy dose, including but not limited to e.g., where 5-MeO-MiPT is administered at a dose above 20 mg, e.g., by oral delivery.

In some embodiments, ibogaine may be administered as a common dose, including but not limited to e.g., a common dose ranging from 15 mg/kg to 22 mg/kg, including e.g., by oral delivery.

Phenethylamines

Useful phenethylamine psychedelic agents include but are not limited to e.g., 3,4,5-trimethoxyphenethylamine (mescaline), 4-allyloxy-3,5-dimethoxyphenethylamine (allylescaline), 3,5-Dimethoxy-4-ethoxyphenethylamine (escaline), 4-Methallyloxy-3,5-dimethoxyphenethylamine (MAL), 4-Propyloxy-3,5-dimethoxyphenethylamine (proscaline), 2,5-dimethoxy-4-bromophenethylamine (2C-B), 4-Chloro-2,5-dimethoxyphenethylamine (2C-C), 2,5-Dimethoxy-4-methylphenethylamine (2C-D), 2,5-Dimethoxy-4-ethylphenethylamine (2C-E), 2,5-Dimethoxy-4-iodophenethylamine (2C-I), 2,5-Dimethoxy-4-propylphenethylamine (2C-P), 2,5-Dimethoxy-4-ethylthiophenethylamine (2C-T-2), 2,5-Dimethoxy-4-propylthiophenethylamine (2C-T-7), 2,5-Dimethoxy-4-ethylfluorothiophenethylamine (2C-T-21), dimethoxybromoamphetamine (DOB), 4-Chloro-2,5-dimethoxyamphetamine (DOC), 4-Chloro-2,5-dimethoxyamphetamine (DOC), 2,5-dimethoxy-4-iodoamphetamine (DOI), 2,5-Dimethoxy-4-methylamphetamine (DOM), 2C-B-NBOMe (25B-NBOMe), 2C-C-NBOMe (25C-NBOMe), 2C-D-NBOMe (25D-NBOMe), 2C-I-NBOMe (25I-NBOMe), 2C-I-NBOH (25N-NBOMe), 2C-C-NBOH (25C-NBOH), 2C-I-NBOH (25I-NBOH), 2-Amino-1-(4-bromo-2,5-dimethoxyphenyl)ethan-1-one (βk-2C-B), and the like.

In some embodiments, mescaline may be administered at or above a threshold dose, including but not limited to e.g., a threshold dose at or above 100 milligrams (mg), including e.g., where oral delivery is employed. In some instances, a threshold dose of mescaline may range from 50 mg to 100 mg, including e.g., by oral delivery. In some embodiments, mescaline may be administered as a light dose, including but not limited to e.g., a light dose ranging from 100 mg to 200 mg, including e.g., by oral delivery. In some embodiments, mescaline may be administered as a common dose, including but not limited to e.g., a common dose ranging from 200 mg to 400 mg, including e.g., by oral delivery. In some embodiments, mescaline may be administered as a strong dose, including but not limited to e.g., a strong dose ranging from 400 mg to 800 mg, including e.g., by oral delivery. In some embodiments, mescaline may be administered as a heavy dose, including but not limited to e.g., where mescaline is administered at a dose above 800 mg, e.g., by oral delivery.

In some embodiments, allylescaline may be administered at or above a threshold dose, including but not limited to e.g., a threshold dose at or above 20 milligrams (mg), including e.g., where oral delivery is employed. In some instances, a threshold dose of allylescaline may range from 15 mg to 20 mg, including e.g., by oral delivery. In some embodiments, allylescaline may be administered as a light dose, including but not limited to e.g., a light dose ranging from 20 mg to 30 mg, including e.g., by oral delivery. In some embodiments, allylescaline may be administered as a common dose, including but not limited to e.g., a common dose ranging from 30 mg to 40 mg, including e.g., by oral delivery. In some embodiments, allylescaline may be administered as a strong dose, including but not limited to e.g., a strong dose ranging from 40 mg to 60 mg, including e.g., by oral delivery. In some embodiments, allylescaline may be administered as a heavy dose, including but not limited to e.g., where allylescaline is administered at a dose above 60 mg, e.g., by oral delivery.

In some embodiments, escaline may be administered at or above a threshold dose, including but not limited to e.g., a threshold dose at or above 30 milligrams (mg), including e.g., where oral delivery is employed. In some instances, a threshold dose of escaline may range from 20 mg to 30 mg, including e.g., by oral delivery. In some embodiments, escaline may be administered as a light dose, including but not limited to e.g., a light dose ranging from 30 mg to 50 mg, including e.g., by oral delivery. In some embodiments, escaline may be administered as a common dose, including but not limited to e.g., a common dose ranging from 50 mg to 100 mg, including e.g., by oral delivery. In some embodiments, escaline may be administered as a strong dose, including but not limited to e.g., a strong dose ranging from 100 mg to 150 mg, including e.g., by oral delivery. In some embodiments, escaline may be administered as a heavy dose, including but not limited to e.g., where escaline is administered at a dose above 150 mg, e.g., by oral delivery.

In some embodiments, MAL may be administered at or above a threshold dose, including but not limited to e.g., a threshold dose at or above 15 milligrams (mg), including e.g., where oral delivery is employed. In some instances, a threshold dose of MAL may range from 5 mg to 15 mg, including e.g., by oral delivery. In some embodiments, MAL may be administered as a light dose, including but not limited to e.g., a light dose ranging from 15 mg to 25 mg, including e.g., by oral delivery. In some embodiments, MAL may be administered as a common dose, including but not limited to e.g., a common dose ranging from 25 mg to 40 mg, including e.g., by oral delivery. In some embodiments, MAL may be administered as a strong dose, including but not limited to e.g., a strong dose ranging from 40 mg to 60 mg, including e.g., by oral delivery. In some embodiments, MAL may be administered as a heavy dose, including but not limited to e.g., where MAL is administered at a dose above 60 mg, e.g., by oral delivery.

In some embodiments, proscaline may be administered at or above a threshold dose, including but not limited to e.g., a threshold dose at or above 15 milligrams (mg), including e.g., where oral delivery is employed. In some instances, a threshold dose of proscaline may range from 10 mg to 15 mg, including e.g., by oral delivery. In some embodiments, proscaline may be administered as a light dose, including but not limited to e.g., a light dose ranging from 15 mg to 30 mg, including e.g., by oral delivery. In some embodiments, proscaline may be administered as a common dose, including but not limited to e.g., a common dose ranging from 30 mg to 40 mg, including e.g., by oral delivery. In some embodiments, proscaline may be administered as a strong dose, including but not limited to e.g., a strong dose ranging from 40 mg to 60 mg, including e.g., by oral delivery. In some embodiments, proscaline may be administered as a heavy dose, including but not limited to e.g., where proscaline is administered at a dose above 60 mg, e.g., by oral delivery.

In some embodiments, 2C-B may be administered at or above a threshold dose, including but not limited to e.g., a threshold dose at or above 10 milligrams (mg), including e.g., where oral delivery is employed. In some instances, a threshold dose of 2C-B may range from 5 mg to 10 mg, including e.g., by oral delivery. In some embodiments, 2C-B may be administered as a light dose, including but not limited to e.g., a light dose ranging from 10 mg to 15 mg, including e.g., by oral delivery. In some embodiments, 2C-B may be administered as a common dose, including but not limited to e.g., a common dose ranging from 15 mg to 25 mg, including e.g., by oral delivery. In some embodiments, 2C-B may be administered as a strong dose, including but not limited to e.g., a strong dose ranging from 25 mg to 45 mg, including e.g., by oral delivery. In some embodiments, 2C-B may be administered as a heavy dose, including but not limited to e.g., where 2C-B is administered at a dose above 45 mg, e.g., by oral delivery.

In some embodiments, 2C-C may be administered at or above a threshold dose, including but not limited to e.g., a threshold dose at or above 15 milligrams (mg), including e.g., where oral delivery is employed. In some instances, a threshold dose of 2C-C may range from 5 mg to 15 mg, including e.g., by oral delivery. In some embodiments, 2C-C may be administered as a light dose, including but not limited to e.g., a light dose ranging from 15 mg to 30 mg, including e.g., by oral delivery. In some embodiments, 2C-C may be administered as a common dose, including but not limited to e.g., a common dose ranging from 30 mg to 50 mg, including e.g., by oral delivery. In some embodiments, 2C-C may be administered as a strong dose, including but not limited to e.g., a strong dose ranging from 50 mg to 90 mg, including e.g., by oral delivery. In some embodiments, 2C-C may be administered as a heavy dose, including but not limited to e.g., where 2C-C is administered at a dose above 90 mg, e.g., by oral delivery.

In some embodiments, 2C-D may be administered at or above a threshold dose, including but not limited to e.g., a threshold dose at or above 10 milligrams (mg), including e.g., where oral delivery is employed. In some instances, a threshold dose of 2C-D may range from 3 mg to 10 mg, including e.g., by oral delivery. In some embodiments, 2C-D may be administered as a light dose, including but not limited to e.g., a light dose ranging from 10 mg to 25 mg, including e.g., by oral delivery. In some embodiments, 2C-D may be administered as a common dose, including but not limited to e.g., a common dose ranging from 25 mg to 50 mg, including e.g., by oral delivery. In some embodiments, 2C-D may be administered as a strong dose, including but not limited to e.g., a strong dose ranging from 50 mg to 100 mg, including e.g., by oral delivery. In some embodiments, 2C-D may be administered as a heavy dose, including but not limited to e.g., where 2C-D is administered at a dose above 100 mg, e.g., by oral delivery.

In some embodiments, 2C-E may be administered at or above a threshold dose, including but not limited to e.g., a threshold dose at or above 5 milligrams (mg), including e.g., where oral delivery is employed. In some instances, a threshold dose of 2C-E may range from 2 mg to 5 mg, including e.g., by oral delivery. In some embodiments, 2C-E may be administered as a light dose, including but not limited to e.g., a light dose ranging from 5 mg to 10 mg, including e.g., by oral delivery. In some embodiments, 2C-E may be administered as a common dose, including but not limited to e.g., a common dose ranging from 10 mg to 15 mg, including e.g., by oral delivery. In some embodiments, 2C-E may be administered as a strong dose, including but not limited to e.g., a strong dose ranging from 15 mg to 30 mg, including e.g., by oral delivery. In some embodiments, 2C-E may be administered as a heavy dose, including but not limited to e.g., where 2C-E is administered at a dose above 30 mg, e.g., by oral delivery.

In some embodiments, 2C-I may be administered at or above a threshold dose, including but not limited to e.g., a threshold dose at or above 5 milligrams (mg), including e.g., where oral delivery is employed. In some instances, a threshold dose of 2C-I may range from 2 mg to 5 mg, including e.g., by oral delivery. In some embodiments, 2C-I may be administered as a light dose, including but not limited to e.g., a light dose ranging from 5 mg to 10 mg, including e.g., by oral delivery. In some embodiments, 2C-I may be administered as a common dose, including but not limited to e.g., a common dose ranging from 10 mg to 20 mg, including e.g., by oral delivery. In some embodiments, 2C-I may be administered as a strong dose, including but not limited to e.g., a strong dose ranging from 20 mg to 30 mg, including e.g., by oral delivery. In some embodiments, 2C-I may be administered as a heavy dose, including but not limited to e.g., where 2C-I is administered at a dose above 30 mg, e.g., by oral delivery.

In some embodiments, 2C-P may be administered at or above a threshold dose, including but not limited to e.g., a threshold dose at or above 3 milligrams (mg), including e.g., where oral delivery is employed. In some instances, a threshold dose of 2C-P may range from 1 mg to 3 mg, including e.g., by oral delivery. In some embodiments, 2C-P may be administered as a light dose, including but not limited to e.g., a light dose ranging from 2 mg to 6 mg, including e.g., by oral delivery. In some embodiments, 2C-P may be administered as a common dose, including but not limited to e.g., a common dose ranging from 6 mg to 10 mg, including e.g., by oral delivery. In some embodiments, 2C-P may be administered as a strong dose, including but not limited to e.g., a strong dose ranging from 10 mg to 16 mg, including e.g., by oral delivery. In some embodiments, 2C-P may be administered as a heavy dose, including but not limited to e.g., where 2C-P is administered at a dose above 16 mg, e.g., by oral delivery.

In some embodiments, 2C-T-2 may be administered at or above a threshold dose, including but not limited to e.g., a threshold dose at or above 5 milligrams (mg), including e.g., where oral delivery is employed. In some instances, a threshold dose of 2C-T-2 may range from 3 mg to 5 mg, including e.g., by oral delivery. In some embodiments, 2C-T-2 may be administered as a light dose, including but not limited to e.g., a light dose ranging from 5 mg to 10 mg, including e.g., by oral delivery. In some embodiments, 2C-T-2 may be administered as a common dose, including but not limited to e.g., a common dose ranging from 10 mg to 20 mg, including e.g., by oral delivery. In some embodiments, 2C-T-2 may be administered as a strong dose, including but not limited to e.g., a strong dose ranging from 20 mg to 30 mg, including e.g., by oral delivery. In some embodiments, 2C-T-2 may be administered as a heavy dose, including but not limited to e.g., where 2C-T-2 is administered at a dose above 25 mg, e.g., by oral delivery.

In some embodiments, 2C-T-7 may be administered at or above a threshold dose, including but not limited to e.g., a threshold dose at or above 10 milligrams (mg), including e.g., where oral delivery is employed. In some instances, a threshold dose of 2C-T-7 may range from 3 mg to 10 mg, including e.g., by oral delivery. In some embodiments, 2C-T-7 may be administered as a light dose, including but not limited to e.g., a light dose ranging from 10 mg to 15 mg, including e.g., by oral delivery. In some embodiments, 2C-T-7 may be administered as a common dose, including but not limited to e.g., a common dose ranging from 15 mg to 25 mg, including e.g., by oral delivery. In some embodiments, 2C-T-7 may be administered as a strong dose, including but not limited to e.g., a strong dose ranging from 25 mg to 40 mg, including e.g., by oral delivery. In some embodiments, 2C-T-7 may be administered as a heavy dose, including but not limited to e.g., where 2C-T-7 is administered at a dose above 40 mg, e.g., by oral delivery.

In some embodiments, 2C-T-21 may be administered at or above a threshold dose, including but not limited to e.g., a threshold dose at or above 5 milligrams (mg), including e.g., where oral delivery is employed. In some embodiments, 2C-T-21 may be administered as a light dose, including but not limited to e.g., a light dose ranging from 5 mg to 10 mg, including e.g., by oral delivery. In some embodiments, 2C-T-21 may be administered as a common dose, including but not limited to e.g., a common dose ranging from 10 mg to 12 mg, including e.g., by oral delivery. In some embodiments, 2C-T-21 may be administered as a strong dose, including but not limited to e.g., a strong dose ranging from 12 mg to 15 mg, including e.g., by oral delivery. In some embodiments, 2C-T-21 may be administered as a heavy dose, including but not limited to e.g., where 2C-T-21 is administered at a dose above 15 mg, e.g., by oral delivery.

In some embodiments, DOB may be administered at or above a threshold dose, including but not limited to e.g., a threshold dose at or above 0.2 milligrams (mg), including e.g., where oral delivery is employed. In some embodiments, DOB may be administered as a light dose, including but not limited to e.g., a light dose ranging from 0.2 mg to 0.75 mg, including e.g., by oral delivery. In some embodiments, DOB may be administered as a common dose, including but not limited to e.g., a common dose ranging from 0.75 mg to 1.75 mg, including e.g., by oral delivery. In some embodiments, DOB may be administered as a strong dose, including but not limited to e.g., a strong dose ranging from 1.75 mg to 3 mg, including e.g., by oral delivery. In some embodiments, DOB may be administered as a heavy dose, including but not limited to e.g., where DOB is administered at a dose above 3 mg, e.g., by oral delivery.

In some embodiments, DOC may be administered at or above a threshold dose, including but not limited to e.g., a threshold dose at or above 1 milligrams (mg), including e.g., where oral delivery is employed. In some instances, a threshold dose of DOC may range from 0.5 mg to 1 mg, including e.g., by oral delivery. In some embodiments, DOC may be administered as a light dose, including but not limited to e.g., a light dose ranging from 1 mg to 2 mg, including e.g., by oral delivery. In some embodiments, DOC may be administered as a common dose, including but not limited to e.g., a common dose ranging from 2 mg to 4 mg, including e.g., by oral delivery. In some embodiments, DOC may be administered as a strong dose, including but not limited to e.g., a strong dose ranging from 4 mg to 6 mg, including e.g., by oral delivery. In some embodiments, DOC may be administered as a heavy dose, including but not limited to e.g., where DOC is administered at a dose above 6 mg, e.g., by oral delivery.

In some embodiments, DOC may be administered at or above a threshold dose, including but not limited to e.g., a threshold dose at or above 0.25 milligrams (mg), including e.g., where insufflated delivery is employed. In some embodiments, DOC may be administered as a light dose, including but not limited to e.g., a light dose ranging from 0.25 mg to 1 mg, including e.g., by insufflated delivery. In some embodiments, DOC may be administered as a common dose, including but not limited to e.g., a common dose ranging from 1 mg to 2 mg, including e.g., by insufflated delivery. In some embodiments, DOC may be administered as a strong dose, including but not limited to e.g., a strong dose ranging from 2 mg to 3.5 mg, including e.g., by insufflated delivery. In some embodiments, DOC may be administered as a heavy dose, including but not limited to e.g., where DOC is administered at a dose above 3.5 mg, e.g., by insufflated delivery.

In some embodiments, DOI may be administered at or above a threshold dose, including but not limited to e.g., a threshold dose at or above 0.5 milligrams (mg), including e.g., where oral delivery is employed. In some embodiments, DOI may be administered as a light dose, including but not limited to e.g., a light dose ranging from 0.5 mg to 1 mg, including e.g., by oral delivery. In some embodiments, DOI may be administered as a common dose, including but not limited to e.g., a common dose ranging from 1 mg to 2 mg, including e.g., by oral delivery. In some embodiments, DOI may be administered as a strong dose, including but not limited to e.g., a strong dose ranging from 2 mg to 3 mg, including e.g., by oral delivery. In some embodiments, DOI may be administered as a heavy dose, including but not limited to e.g., where DOI is administered at a dose above 3 mg, e.g., by oral delivery.

In some embodiments, DOM may be administered at or above a threshold dose, including but not limited to e.g., a threshold dose at or above 1 milligrams (mg), including e.g., where oral delivery is employed. In some instances, a threshold dose of DOM may range from 0.5 mg to 1 mg, including e.g., by oral delivery. In some embodiments, DOM may be administered as a light dose, including but not limited to e.g., a light dose ranging from 1 mg to 3 mg, including e.g., by oral delivery. In some embodiments, DOM may be administered as a common dose, including but not limited to e.g., a common dose ranging from 3 mg to 5 mg, including e.g., by oral delivery. In some embodiments, DOM may be administered as a strong dose, including but not limited to e.g., a strong dose ranging from 5 mg to 10 mg, including e.g., by oral delivery. In some embodiments, DOM may be administered as a heavy dose, including but not limited to e.g., where DOM is administered at a dose above 10 mg, e.g., by oral delivery.

In some embodiments, βk-2C-B may be administered at or above a threshold dose, including but not limited to e.g., a threshold dose at or above 60 milligrams (mg), including e.g., where oral delivery is employed. In some instances, a threshold dose of βk-2C-B may range from 50 mg to 60 mg, including e.g., by oral delivery. In some embodiments, βk-2C-B may be administered as a light dose, including but not limited to e.g., a light dose ranging from 60 mg to 80 mg, including e.g., by oral delivery. In some embodiments, βk-2C-B may be administered as a common dose, including but not limited to e.g., a common dose ranging from 80 mg to 100 mg, including e.g., by oral delivery. In some embodiments, βk-2C-B may be administered as a strong dose, including but not limited to e.g., a strong dose ranging from 100 mg to 150 mg, including e.g., by oral delivery. In some embodiments, βk-2C-B may be administered as a heavy dose, including but not limited to e.g., where βk-2C-B is administered at a dose above 150 mg, e.g., by oral delivery.

In some embodiments, 25B-NBOMe may be administered at or above a threshold dose, including but not limited to e.g., a threshold dose at or above 100 micrograms (ug), including e.g., where sublingual delivery is employed. In some instances, a threshold dose of 25B-NBOMe may range from 50 ug to 100 ug, including e.g., by sublingual delivery. In some embodiments, 25B-NBOMe may be administered as a light dose, including but not limited to e.g., a light dose ranging from 100 ug to 300 ug, including e.g., by sublingual delivery. In some embodiments, 25B-NBOMe may be administered as a common dose, including but not limited to e.g., a common dose ranging from 300 ug to 500 ug, including e.g., by sublingual delivery. In some embodiments, 25B-NBOMe may be administered as a strong dose, including but not limited to e.g., a strong dose ranging from 500 ug to 700 ug, including e.g., by sublingual delivery.

In some embodiments, 25C-NBOMe may be administered at or above a threshold dose, including but not limited to e.g., a threshold dose at or above 100 micrograms (ug), including e.g., where sublingual delivery is employed. In some instances, a threshold dose of 25C-NBOMe may range from 50 ug to 100 ug, including e.g., by sublingual delivery. In some embodiments, 25C-NBOMe may be administered as a light dose, including but not limited to e.g., a light dose ranging from 100 ug to 300 ug, including e.g., by sublingual delivery. In some embodiments, 25C-NBOMe may be administered as a common dose, including but not limited to e.g., a common dose ranging from 300 ug to 500 ug, including e.g., by sublingual delivery. In some embodiments, 25C-NBOMe may be administered as a strong dose, including but not limited to e.g., a strong dose ranging from 500 ug to 700 ug, including e.g., by sublingual delivery.

In some embodiments, 25D-NBOMe may be administered at or above a threshold dose, including but not limited to e.g., a threshold dose at or above 300 micrograms (ug), including e.g., where sublingual delivery is employed. In some instances, a threshold dose of 25D-NBOMe may range from ug to 300 ug, including e.g., by sublingual delivery. In some embodiments, 25D-NBOMe may be administered as a light dose, including but not limited to e.g., a light dose ranging from 300 ug to 800 ug, including e.g., by sublingual delivery. In some embodiments, 25D-NBOMe may be administered as a common dose, including but not limited to e.g., a common dose ranging from 800 ug to 1000 ug, including e.g., by sublingual delivery. In some embodiments, 25D-NBOMe may be administered as a strong dose, including but not limited to e.g., a strong dose ranging from 1000 ug to 1200 ug, including e.g., by sublingual delivery.

In some embodiments, 25I-NBOMe may be administered at or above a threshold dose, including but not limited to e.g., a threshold dose at or above 200 micrograms (ug), including e.g., where sublingual delivery is employed. In some instances, a threshold dose of 25I-NBOMe may range from 50 ug to 200 ug, including e.g., by sublingual delivery. In some embodiments, 25I-NBOMe may be administered as a light dose, including but not limited to e.g., a light dose ranging from 200 ug to 500 ug, including e.g., by sublingual delivery. In some embodiments, 25I-NBOMe may be administered as a common dose, including but not limited to e.g., a common dose ranging from 500 ug to 700 ug, including e.g., by sublingual delivery. In some embodiments, 25I-NBOMe may be administered as a strong dose, including but not limited to e.g., a strong dose ranging from 700 ug to 1000 ug, including e.g., by sublingual delivery.

In some embodiments, 25N-NBOMe may be administered at or above a threshold dose, including but not limited to e.g., a threshold dose at or above 200 micrograms (ug), including e.g., where sublingual delivery is employed. In some instances, a threshold dose of 25N-NBOMe may range from 50 ug to 200 ug, including e.g., by sublingual delivery. In some embodiments, 25N-NBOMe may be administered as a light dose, including but not limited to e.g., a light dose ranging from 200 ug to 500 ug, including e.g., by sublingual delivery. In some embodiments, 25N-NBOMe may be administered as a common dose, including but not limited to e.g., a common dose ranging from 500 ug to 900 ug, including e.g., by sublingual delivery. In some embodiments, 25N-NBOMe may be administered as a strong dose, including but not limited to e.g., a strong dose ranging from 900 ug to 1400 ug, including e.g., by sublingual delivery.

In some embodiments, 25C-NBOH may be administered at or above a threshold dose, including but not limited to e.g., a threshold dose at or above 250 micrograms (ug), including e.g., where sublingual delivery is employed. In some instances, a threshold dose of 25C-NBOH may range from 100 ug to 250 ug, including e.g., by sublingual delivery. In some embodiments, 25C-NBOH may be administered as a light dose, including but not limited to e.g., a light dose ranging from 250 ug to 500 ug, including e.g., by sublingual delivery. In some embodiments, 25C-NBOH may be administered as a common dose, including but not limited to e.g., a common dose ranging from 500 ug to 750 ug, including e.g., by sublingual delivery. In some embodiments, 25C-NBOH may be administered as a strong dose, including but not limited to e.g., a strong dose ranging from 750 ug to 1000 ug, including e.g., by sublingual delivery.

In some embodiments, 25I-NBOH may be administered at or above a threshold dose, including but not limited to e.g., a threshold dose at or above 200 micrograms (ug), including e.g., where sublingual delivery is employed. In some instances, a threshold dose of 25I-NBOH may range from 50 ug to 200 ug, including e.g., by sublingual delivery. In some embodiments, 25I-NBOH may be administered as a light dose, including but not limited to e.g., a light dose ranging from 200 ug to 500 ug, including e.g., by sublingual delivery. In some embodiments, 25I-NBOH may be administered as a common dose, including but not limited to e.g., a common dose ranging from 500 ug to 900 ug, including e.g., by sublingual delivery. In some embodiments, 25I-NBOH may be administered as a strong dose, including but not limited to e.g., a strong dose ranging from 900 ug to 1400 ug, including e.g., by sublingual delivery.

Entactogens

Enactogens may vary in the specific mode of action through which the agent functions and thus, enactogens may include e.g., benzofuran enactogens, phenethylamine enactogens, aminoindane enactogens, amphetamine enactogens, cathinone enactogens, etc. Useful enactogens include but are not limited to e.g., benzofuran entactogen 5-(2-Aminopropyl)benzofuran (5-APB), benzofuran entactogen 5-(2-methylaminopropyl)benzofuran (5-MAPB), phenethylamine entactogen 6-(2-Aminopropyl)benzofuran (6-APB), phenethylamine entactogen 6-(2-aminopropyl)-2,3-dihydrobenzofuran (6-APDB), aminoindane entactogen 5,6-Methylenedioxy-2-aminoindane (MDAI), amphetamine entactogen 3,4-Methylenedioxyamphetamine (MDA), amphetamine entactogen 3,4-Methylenedioxy-N-ethylamphetamine (MDEA), phenethylamine entactogen 3,4-methylenedioxymethamphetamine (MDMA), cathinone entactogen 3,4-Methylenedioxy-N-methcathinone (βk-MDMA), and the like.

In some embodiments, 5-APB may be administered at or above a threshold dose, including but not limited to e.g., a threshold dose at or above 40 milligrams (mg), including e.g., where oral delivery is employed. In some instances, a threshold dose of 5-APB may range from 20 mg to 40 mg, including e.g., by oral delivery. In some embodiments, 5-APB may be administered as a light dose, including but not limited to e.g., a light dose ranging from 40 mg to 60 mg, including e.g., by oral delivery. In some embodiments, 5-APB may be administered as a common dose, including but not limited to e.g., a common dose ranging from 60 mg to 80 mg, including e.g., by oral delivery. In some embodiments, 5-APB may be administered as a strong dose, including but not limited to e.g., a strong dose ranging from 80 mg to 100 mg, including e.g., by oral delivery. In some embodiments, 5-APB may be administered as a heavy dose, including but not limited to e.g., where 5-APB is administered at a dose above 100 mg, e.g., by oral delivery.

In some embodiments, 5-MAPB may be administered at or above a threshold dose, including but not limited to e.g., a threshold dose at or above 40 milligrams (mg), including e.g., where oral delivery is employed. In some instances, a threshold dose of 5-MAPB may range from 20 mg to 40 mg, including e.g., by oral delivery. In some embodiments, 5-MAPB may be administered as a light dose, including but not limited to e.g., a light dose ranging from 40 mg to 60 mg, including e.g., by oral delivery. In some embodiments, 5-MAPB may be administered as a common dose, including but not limited to e.g., a common dose ranging from 60 mg to 80 mg, including e.g., by oral delivery. In some embodiments, 5-MAPB may be administered as a strong dose, including but not limited to e.g., a strong dose ranging from 80 mg to 100 mg, including e.g., by oral delivery. In some embodiments, 5-MAPB may be administered as a heavy dose, including but not limited to e.g., where 5-MAPB is administered at a dose above 100 mg, e.g., by oral delivery.

In some embodiments, 6-APB may be administered at or above a threshold dose, including but not limited to e.g., a threshold dose at or above 30 milligrams (mg), including e.g., where oral delivery is employed. In some instances, a threshold dose of 6-APB may range from 15 mg to 30 mg, including e.g., by oral delivery. In some embodiments, 6-APB may be administered as a light dose, including but not limited to e.g., a light dose ranging from 30 mg to 60 mg, including e.g., by oral delivery. In some embodiments, 6-APB may be administered as a common dose, including but not limited to e.g., a common dose ranging from 60 mg to 90 mg, including e.g., by oral delivery. In some embodiments, 6-APB may be administered as a strong dose, including but not limited to e.g., a strong dose ranging from 90 mg to 120 mg, including e.g., by oral delivery. In some embodiments, 6-APB may be administered as a heavy dose, including but not limited to e.g., where 6-APB is administered at a dose above 120 mg, e.g., by oral delivery.

In some embodiments, 6-APDB may be administered at or above a threshold dose, including but not limited to e.g., a threshold dose at or above 30 milligrams (mg), including e.g., where oral delivery is employed. In some instances, a threshold dose of 6-APDB may range from 20 mg to 30 mg, including e.g., by oral delivery. In some embodiments, 6-APDB may be administered as a light dose, including but not limited to e.g., a light dose ranging from 30 mg to 70 mg, including e.g., by oral delivery. In some embodiments, 6-APDB may be administered as a common dose, including but not limited to e.g., a common dose ranging from 70 mg to 100 mg, including e.g., by oral delivery. In some embodiments, 6-APDB may be administered as a strong dose, including but not limited to e.g., a strong dose ranging from 100 mg to 130 mg, including e.g., by oral delivery. In some embodiments, 6-APDB may be administered as a heavy dose, including but not limited to e.g., where 6-APDB is administered at a dose above 130 mg, e.g., by oral delivery.

In some embodiments, MDAI may be administered at or above a threshold dose, including but not limited to e.g., a threshold dose at or above 40 milligrams (mg), including e.g., where oral delivery is employed. In some embodiments, MDAI may be administered as a light dose, including but not limited to e.g., a light dose ranging from 40 mg to 100 mg, including e.g., by oral delivery. In some embodiments, MDAI may be administered as a common dose, including but not limited to e.g., a common dose ranging from 100 mg to 175 mg, including e.g., by oral delivery. In some embodiments, MDAI may be administered as a strong dose, including but not limited to e.g., a strong dose ranging from 175 mg to 300 mg, including e.g., by oral delivery. In some embodiments, MDAI may be administered as a heavy dose, including but not limited to e.g., where MDAI is administered at a dose above 300 mg, e.g., by oral delivery.

In some embodiments, MDA may be administered at or above a threshold dose, including but not limited to e.g., a threshold dose at or above 40 milligrams (mg), including e.g., where oral delivery is employed. In some instances, a threshold dose of MDA may range from 20 mg to 40 mg, including e.g., by oral delivery. In some embodiments, MDA may be administered as a light dose, including but not limited to e.g., a light dose ranging from 40 mg to 60 mg, including e.g., by oral delivery. In some embodiments, MDA may be administered as a common dose, including but not limited to e.g., a common dose ranging from 60 mg to 100 mg, including e.g., by oral delivery. In some embodiments, MDA may be administered as a strong dose, including but not limited to e.g., a strong dose ranging from 100 mg to 145 mg, including e.g., by oral delivery. In some embodiments, MDA may be administered as a heavy dose, including but not limited to e.g., where MDA is administered at a dose above 145 mg, e.g., by oral delivery.

In some embodiments, MDEA may be administered at or above a threshold dose, including but not limited to e.g., a threshold dose at or above 70 milligrams (mg), including e.g., where oral delivery is employed. In some instances, a threshold dose of MDEA may range from 50 mg to 70 mg, including e.g., by oral delivery. In some embodiments, MDEA may be administered as a light dose, including but not limited to e.g., a light dose ranging from 70 mg to 120 mg, including e.g., by oral delivery. In some embodiments, MDEA may be administered as a common dose, including but not limited to e.g., a common dose ranging from 120 mg to 180 mg, including e.g., by oral delivery. In some embodiments, MDEA may be administered as a strong dose, including but not limited to e.g., a strong dose ranging from 180 mg to 225 mg, including e.g., by oral delivery. In some embodiments, MDEA may be administered as a heavy dose, including but not limited to e.g., where MDEA is administered at a dose above 225 mg, e.g., by oral delivery.

In some embodiments, MDMA may be administered at or above a threshold dose, including but not limited to e.g., a threshold dose at or above 40 milligrams (mg), including e.g., where oral delivery is employed. In some embodiments, MDMA may be administered as a light dose, including but not limited to e.g., a light dose ranging from 40 mg to 70 mg, including e.g., by oral delivery. In some embodiments, MDMA may be administered as a common dose, including but not limited to e.g., a common dose ranging from 70 mg to 140 mg, including e.g., by oral delivery. In some embodiments, MDMA may be administered as a strong dose, including but not limited to e.g., a strong dose ranging from 140 mg to 180 mg, including e.g., by oral delivery. In some embodiments, MDMA may be administered as a heavy dose, including but not limited to e.g., where MDMA is administered at a dose above 180 mg, e.g., by oral delivery.

In some embodiments, βk-MDMA may be administered at or above a threshold dose, including but not limited to e.g., a threshold dose at or above 75 milligrams (mg), including e.g., where oral delivery is employed. In some embodiments, βk-MDMA may be administered as a light dose, including but not limited to e.g., a light dose ranging from 75 mg to 150 mg, including e.g., by oral delivery. In some embodiments, βk-MDMA may be administered as a common dose, including but not limited to e.g., a common dose ranging from 150 mg to 225 mg, including e.g., by oral delivery. In some embodiments, βk-MDMA may be administered as a strong dose, including but not limited to e.g., a strong dose ranging from 225 mg to 325 mg, including e.g., by oral delivery. In some embodiments, βk-MDMA may be administered as a heavy dose, including but not limited to e.g., where βk-MDMA is administered at a dose above 325 mg, e.g., by oral delivery.

Non-Traditional and Atypical Psychedelics

Non-traditional and atypical psychedelic agents include agents that are not lysergamide, tryptamine, or phenethylamine psychedelic agents or at least not solely a lysergamide, a tryptamine, or a phenethylamine. Such non-traditional and atypical psychedelic agents may vary in the specific mode of action through which the agent functions or such agents may function through multiple modes. For example, non-traditional psychedelic agents may be amphetamines, benzofurans, combination phenethylamine and benzodihydrodifurans, substituted combination amphetamine and phenethylamines, and the like. Useful non-traditional psychedelic agents include but are not limited to e.g., 8-bromo-2,3,6,7-benzo-dihydro-difuran-ethylamine (2C-B-FLY), 3,5-Dimethoxy-4-ethoxyamphetamine (3C-E), 5-Methoxy-N,N-diisopropylbenzofuranethyl-amine (5-MeO-DiBF), 8-bromo-4-(2-aminopropyl)benzodifuran (B-DFLY), 2,4,5-Trimethoxyamphetamine (TMA-2), 2,4,6-Trimethoxyamphetamine (TMA-6), and the like. Atypical psychedelic agents may be K-opioid receptor agonists, including but not limited to e.g., salvinorin A, 2-O-methoxymethylsalvinorin B (2-MMSB), and the like.

In some embodiments, 2C-B-FLY may be administered at or above a threshold dose, including but not limited to e.g., a threshold dose at or above 5 milligrams (mg), including e.g., where oral delivery is employed. In some instances, a threshold dose of 2C-B-FLY may range from 2 mg to 5 mg, including e.g., by oral delivery. In some embodiments, 2C-B-FLY may be administered as a light dose, including but not limited to e.g., a light dose ranging from 5 mg to 10 mg, including e.g., by oral delivery. In some embodiments, 2C-B-FLY may be administered as a common dose, including but not limited to e.g., a common dose ranging from 10 mg to 18 mg, including e.g., by oral delivery. In some embodiments, 2C-B-FLY may be administered as a strong dose, including but not limited to e.g., a strong dose ranging from 18 mg to 25 mg, including e.g., by oral delivery. In some embodiments, 2C-B-FLY may be administered as a heavy dose, including but not limited to e.g., where 2C-B-FLY is administered at a dose above 25 mg, e.g., by oral delivery.

In some embodiments, 3C-E may be administered at or above a threshold dose, including but not limited to e.g., a threshold dose at or above 30 milligrams (mg), including e.g., where oral delivery is employed. In some instances, a threshold dose of 3C-E may range from 20 mg to 30 mg, including e.g., by oral delivery. In some embodiments, 3C-E may be administered as a light dose, including but not limited to e.g., a light dose ranging from 30 mg to 40 mg, including e.g., by oral delivery. In some embodiments, 3C-E may be administered as a common dose, including but not limited to e.g., a common dose ranging from 40 mg to 60 mg, including e.g., by oral delivery. In some embodiments, 3C-E may be administered as a strong dose, including but not limited to e.g., a strong dose ranging from 60 mg to 80 mg, including e.g., by oral delivery. In some embodiments, 3C-E may be administered as a heavy dose, including but not limited to e.g., where 3C-E is administered at a dose above 80 mg, e.g., by oral delivery.

In some embodiments, 5-MeO-DiBF may be administered at or above a threshold dose, including but not limited to e.g., a threshold dose at or above 50 milligrams (mg), including e.g., where oral delivery is employed. In some instances, a threshold dose of 5-MeO-DiBF may range from 20 mg to 50 mg, including e.g., by oral delivery. In some embodiments, 5-MeO-DiBF may be administered as a light dose, including but not limited to e.g., a light dose ranging from 50 mg to 80 mg, including e.g., by oral delivery. In some embodiments, 5-MeO-DiBF may be administered as a common dose, including but not limited to e.g., a common dose ranging from 80 mg to 110 mg, including e.g., by oral delivery. In some embodiments, 5-MeO-DiBF may be administered as a strong dose, including but not limited to e.g., a strong dose ranging from 110 mg to 140 mg, including e.g., by oral delivery. In some embodiments, 5-MeO-DiBF may be administered as a heavy dose, including but not limited to e.g., where 5-MeO-DiBF is administered at a dose above 140 mg, e.g., by oral delivery.

In some embodiments, B-DFLY may be administered at or above a threshold dose, including but not limited to e.g., a threshold dose at or above 100 milligrams (mg), including e.g., where oral delivery is employed. In some instances, a threshold dose of B-DFLY may range from 75 mg to 100 mg, including e.g., by oral delivery. In some embodiments, B-DFLY may be administered as a light dose, including but not limited to e.g., a light dose ranging from 100 mg to 300 mg, including e.g., by oral delivery. In some embodiments, B-DFLY may be administered as a common dose, including but not limited to e.g., a common dose ranging from 300 mg to 500 mg, including e.g., by oral delivery. In some embodiments, B-DFLY may be administered as a strong dose, including but not limited to e.g., a strong dose ranging from 500 mg to 750 mg, including e.g., by oral delivery. In some embodiments, B-DFLY may be administered as a heavy dose, including but not limited to e.g., where B-DFLY is administered at a dose above 750 mg, e.g., by oral delivery.

In some embodiments, TMA-2 may be administered at or above a threshold dose, including but not limited to e.g., a threshold dose at or above 10 milligrams (mg), including e.g., where oral delivery is employed. In some instances, a threshold dose of TMA-2 may range from 5 mg to 10 mg, including e.g., by oral delivery. In some embodiments, TMA-2 may be administered as a light dose, including but not limited to e.g., a light dose ranging from 10 mg to 20 mg, including e.g., by oral delivery. In some embodiments, TMA-2 may be administered as a common dose, including but not limited to e.g., a common dose ranging from 20 mg to 40 mg, including e.g., by oral delivery. In some embodiments, TMA-2 may be administered as a strong dose, including but not limited to e.g., a strong dose ranging from 40 mg to 60 mg, including e.g., by oral delivery. In some embodiments, TMA-2 may be administered as a heavy dose, including but not limited to e.g., where TMA-2 is administered at a dose above 60 mg, e.g., by oral delivery.

In some embodiments, TMA-6 may be administered at or above a threshold dose, including but not limited to e.g., a threshold dose at or above 10 milligrams (mg), including e.g., where oral delivery is employed. In some instances, a threshold dose of TMA-6 may range from 5 mg to 10 mg, including e.g., by oral delivery. In some embodiments, TMA-6 may be administered as a light dose, including but not limited to e.g., a light dose ranging from 10 mg to 20 mg, including e.g., by oral delivery. In some embodiments, TMA-6 may be administered as a common dose, including but not limited to e.g., a common dose ranging from 20 mg to 35 mg, including e.g., by oral delivery. In some embodiments, TMA-6 may be administered as a strong dose, including but not limited to e.g., a strong dose ranging from 35 mg to 50 mg, including e.g., by oral delivery. In some embodiments, TMA-6 may be administered as a heavy dose, including but not limited to e.g., where TMA-6 is administered at a dose above 50 mg, e.g., by oral delivery.

In some instances, useful psychedelic agents of the present disclosure may include those agents that result in reduced inflammation in a subject following one or more administrations of the agent. The mechanism by which such reduced inflammation is mediated by a subject psychedelic agent may vary and may, in some instances, include modulation of phosphatidylinositol-4,5-bisphosphate 3-kinase (PI3K) signaling through one or more 5-HT receptors, modulation of sigma receptors (e.g., sigma-1 receptor (σ1R)), modulation of lymphocyte functions, or any combination thereof. Inflammation, e.g., reduced inflammation after psychedelic agent administration, may be measured using any convenient and appropriate method, including e.g., assessing type I interferon (IFN) levels; inflammatory cytokine and/or chemokine levels (IFNβ, IL-8, IL-1β, IL-6, TNFα, etc.); and the like. Such inflammation reducing psychedelic agents may include but are not limited to e.g., DMT, DOI, LSD, MDMA, psilocin, and the like. Furthermore, any agent or class of agents, including e.g., those described herein, may be readily evaluated for inflammation reducing effects, including e.g., by administering the agent to a subject and measuring the resulting inflammation level.

Psychedelic agents, employed in the methods of the present disclosure, may be administered alone or may be administered as part of a pharmaceutical composition. For example, in some instances, the subject psychedelic agent or agents may be formulated together with a pharmaceutically acceptable excipient. In some instances, one or more additional active ingredients may be included in the composition. In some instances, the psychedelic agent or agents may be the sole therapeutic agent of the composition.

Compositions useful for administering one or more psychedelic agents of the present disclosure may, in some instances, include obtained and/or prepared foodstuffs that include the one or more psychedelic agents, such as but not limited to e.g., mushrooms, brews, chewables, baked goods, confections, and the like. Non-limiting examples of useful obtained or prepared foodstuffs include ayahuasca, dried psilocybin mushrooms, and the like.

Any convenient and appropriate route of administration may be employed in delivering a psychedelic agent to a subject, including but not limited to e.g., oral, inhalation (e.g., smoked, vaporized, etc.), intra-arteria injection/infusion, intravenous injection/infusion, intramuscular injection, as well as topical routes, including e.g., transdermal, transmucosal (e.g., sublingual, insufflation, and/or buccal), and the like. In some instances, a delivery device configured for delivering the one or more psychedelic agents according to any desired and appropriate route of delivery may be employed.

Different devices and systems for applying one or more pharmacological agents to a subject which may be adapted for use for the delivery of one or more psychedelic agents of the subject methods include embodiments configured to deliver pharmacological agent(s) using any of the methods described herein.

Embodiments may include an implantable or external pharmacological delivery device such as, but not limited to, pumps, epidural injectors, syringes or other injection apparatus, catheter and/or reservoir operatively associated with a catheter, etc. For example, in certain embodiments a delivery device employed to deliver at least one psychedelic agent to a subject may be a pump, syringe, catheter or reservoir operably associated with a connecting device such as a catheter, tubing, or the like. Containers suitable for delivery of at least one psychedelic agent to a psychedelic agent administration device include instruments of containment that may be used to deliver, place, attach, and/or insert the at least one psychedelic agent into the delivery device for administration of the psychedelic agent to a subject and include, but are not limited to, vials, ampules, tubes, capsules, bottles, syringes and bags.

Devices and systems for applying at least one pharmacological agent to a subject and which may be adapted for use in the subject methods are described, e.g., in U.S. Pat. Nos. 7,363,076; 6,503,532; 5,302,395; 5,262,165; 5,248,501; 5,232,702; 5,230,896; 5,227,169; 5,212,199; 5,202,125; 5,173,302; 5,154,922; 5,139,786; 5,122,383; 5,023,252; 4,978,532; 5,324,521; 5,306,503; 5,302,395; 5,296,230; 5,286,491; 5,252,334; 5,248,501; 5,230,896; 5,227,169; 5,212,199; 5,202,125; 5,173,302; 5,171,576; 5,139,786; 5,133,972; 5,122,383; 5,120,546; 5,118,509; 5,077,054; 5,066,494; 5,049,387; 5,028,435; 5,023,252; 5,000,956; 4,911,916; 4,898,734; 4,883,669; 4,882,377; 4,840,796; 4,818,540; 4,814,173; 4,806,341; 4,789,547; 4,786,277; 4,702,732; 4,690,683; 4,627,429; 4,585,452; U.S. patent application Ser. Nos. 10/748,897; 10/748,976; 10/871,366; 10/846,486 10/917,270; 10/962,190; 11/060,643 11/251,629; 11/238,108; 11/592,027; 60/654,139; 60/702,776; and elsewhere, the disclosures of which are herein incorporated by reference.

Assessments

As summarized above, in some instances, methods of the present disclosure may include one or more assessments. Useful assessments may be employed at one or more various points in the method, including e.g., before, during and/or after administration of a psychedelic agent to the subject. A treatment protocol for a subject having a food allergy condition may include assessing whether the food allergy condition is present in the subject. In some instances, assessments of a subject may be employed to determine or otherwise influence a treatment protocol for a food allergy condition of the subject. In some instances, assessments may be employed to determine the effectiveness of a treatment.

Any convenient and appropriate method of assessment may be employed in the herein described procedures, including but not limited to e.g., allergy assessments, inflammation assessments, and the like. Useful allergy assessments include but are not limited to e.g., oral food allergy challenge (OFC) (e.g., open-food challenge, single-blind food challenge, double-blind, placebo-controlled food challenge (DBPCFC), and the like); skin prick tests; blood tests; trial elimination diet tests; and the like. Useful evaluations are further described in "*Guidelines for the Diagnosis and Management of Food Allergy in the United States*" (Boyce et al., *J Allergy Clin Immunol.* (2010) 126(6 0): S1-58; the disclosure of which is incorporated herein by reference in its entirety. In some embodiments, food allergy assessment may be employed to diagnose a subject with a food allergy condition or a subject may have been previously diagnosed with a food allergy condition according to a food allergy assessment previously performed.

After an assessment of a subject's food allergy condition, e.g., an assessment of whether the subject has a food allergy condition, is conducted, a determination of a treatment protocol for the subject for the condition may be made. The treatment protocol may include administering to the subject one or more psychedelic agents. As described above, treating a subject through the administration of a psychedelic agent may include treating the subject using essentially any convenient and appropriate psychedelic agent, or a combination of the psychedelic agents, including but not limited to e.g., those described or incorporated by reference herein. In some instances, psychedelic agent administration may be employed where a conventional treatment for the food allergy is insufficient, unsuccessful, and/or contraindicated. For example, in some instances, psychedelic agent administration may be employed where it is determined that oral immunotherapy is insufficient, unsuccessful, and/or contraindicated to treat the food allergy condition of a subject, e.g., the subject may be determined to be refractory to oral immunotherapy for a food allergy condition.

The treatment protocol may also include specifically excluding psychedelic agent administration if the subject does not have a food allergy condition or if the determining professional(s) determine that psychedelic administration is unnecessary or contraindicated. In specifically excluding psychedelic agent administration, a determination may be made to not perform psychedelic agent administration to the subject if the subject does not have a food allergy condition, has a condition where psychedelic administration would be contraindicated, has a food allergy condition that is treatable by another means, etc. Such a determination may include a determination that oral immunotherapy is sufficient to treat the food allergy.

The assessment and determination steps, e.g., as described above, may be conducted by one or more of a doctor, nurse, medical professional or individual with appropriate expertise. The assessing professional(s) may be the same as or different from the determining professional(s), e.g., as desired.

In some instances, useful assessments may include one or more in vitro assessments, e.g., performed on a sample obtained from the subject. Useful in vitro assessments may include in vitro allergy testing, such as but not limited to e.g., in vitro tests for detecting allergen-specific IgE. In vitro allergy testing may include collecting a sample from the subject, e.g., a blood and/or serum sample, and evaluating the presence of an analyte, e.g., allergen-specific IgE, in the sample to assess the subject for the food allergy condition.

Such assessments may be qualitative or quantitative depending on the particular context. For example, in some instances, an assessment, including allergy assessments of the subject (e.g., an OFC assessment) or an in vitro assessment (e.g., allergen-specific IgE evaluation), may indicate an improvement in the subject's food allergy condition. Such improvements may be qualitative or quantitative. For example, in some instances, assessing a food allergy condition of a subject may indicate a quantitative improvement, such as e.g., at least a 5% improvement in the food allergy condition of the subject. Measured improvements may vary according to the method employed to assess a subject's food allergy condition. For example, in some instances, an assessment may indicate at least a 5% increase in food antigen tolerance following a method of treatment as described herein, e.g., as measured by an OFC. In some instances, an assessment may indicate at least a 5% decrease in the presence allergen-specific IgE following a method of treatment as described herein, e.g., as measured by an in vitro assessment.

Various assessments may be employed to measure one or more conditions of a subject before, during, and/or after administration of a psychedelic agent. In some instances, a subject may be continuously or semi-continuously assessed (i.e., monitored) during one or more, including all, portions of a method of treatment described herein.

In some instances, a subject may undergo a psychological evaluation. For example, a subject may be tested to obtain a psychological evaluation of the subject prior to the administering. In some embodiments, administration of a psychedelic agent and/or the choice of agent employed may be contingent on the results of the psychological evaluation. In some instances, a psychological evaluation may be performed during and/or after administration of one or more psychedelic agents to the subject. Useful psychological evaluations will vary and may include, but are not limited to e.g., one or more of a psychotic history evaluation, a mania evaluation, and a personality disorder evaluation (e.g., an evaluation for borderline personality disorder).

The following example(s) is/are offered by way of illustration and not by way of limitation.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Evaluating Psychedelic Agent-Mediated Reduction of Food Allergy Severity Human subjects with known food allergies are subjected to an oral food challenge to determine the baseline severity of each subject's allergy. Having assessed the severity of each subject's allergy, the subjects are divided into two age- and allergy-severity matched groups. Group A is prescribed and administered a treatment schedule consisting of a weekly strong dose of a psychedelic agent (e.g., LSD, psilocin or DMT) for four weeks. Group B is prescribed and administered a weekly non-psychedelic active placebo (e.g., niacin or methylphenidate) for four weeks. One week after the end of the treatment trial, the subjects of both groups are subjected to an oral food challenge to determine the end-point severity of each subject's allergy. Comparison of the end-point results demonstrates a decrease in allergen sensitivity in Group A and such decrease is greater than any decrease observed in the control group (Group B).

Although the foregoing invention has been described in some detail by way of illustration and example for purposes of clarity of understanding, it is readily apparent to those of ordinary skill in the art in light of the teachings of this invention that certain changes and modifications may be made thereto without departing from the spirit or scope of the appended claims.

Accordingly, the preceding merely illustrates the principles of the invention. It will be appreciated that those skilled in the art will be able to devise various arrangements which, although not explicitly described or shown herein, embody the principles of the invention and are included within its spirit and scope. Furthermore, all examples and conditional language recited herein are principally intended to aid the reader in understanding the principles of the invention and the concepts contributed by the inventors to furthering the art, and are to be construed as being without limitation to such specifically recited examples and conditions. Moreover, all statements herein reciting principles, aspects, and embodiments of the invention as well as specific examples thereof, are intended to encompass both structural and functional equivalents thereof. Additionally, it is intended that such equivalents include both currently known equivalents and equivalents developed in the future, i.e., any elements developed that perform the same function, regardless of structure. Moreover, nothing disclosed herein is intended to be dedicated to the public regardless of whether such disclosure is explicitly recited in the claims.

The scope of the present invention, therefore, is not intended to be limited to the exemplary embodiments shown and described herein. Rather, the scope and spirit of present invention is embodied by the appended claims. In the claims, 35 U.S.C. § 112(f) or 35 U.S.C. § 112(6) is expressly defined as being invoked for a limitation in the claim only when the exact phrase "means for" or the exact phrase "step for" is recited at the beginning of such limitation in the claim; if such exact phrase is not used in a limitation in the claim, then 35 U.S.C. § 112 (f) or 35 U.S.C. § 112(6) is not invoked.

What is claimed is:

1. A method of treating a food allergy condition in a subject in need thereof, the method comprising administering to the subject an amount of a lysergamide psychedelic agent effective to treat the subject for the food allergy condition.

2. The method according to claim 1, wherein the subject has been diagnosed with the food allergy condition.

3. The method according to claim 2, wherein the method comprises diagnosing the subject with the food allergy condition.

4. The method according to claim 3, wherein the diagnosing comprises an antigen challenge.

5. The method according to claim 1, wherein the method further comprises an antigen challenge before and/or during the administering.

6. The method according to claim 1, wherein the method comprises a therapeutic regimen comprising multiple rounds of administering the psychedelic agent.

7. The method according to claim 6, wherein the therapeutic regimen comprises a holiday period.

8. The method according to claim 1, wherein the method comprises an abstinent period prior to the administering.

9. The method according to claim 8, wherein during the abstinent period the subject abstains from one or more of over-the-counter medications, prescription medications, alcohol and illicit drugs.

10. The method according to claim 9, wherein the prescription medications comprise psychiatric drugs.

11. The method according to claim 1, wherein the lysergamide is selected from lysergic acid diethylamide (LSD) and d-lysergic acid amide (LSA).

12. The method according to claim 1, wherein the psychedelic agent is administered in a composition.

13. The method according to claim 12, wherein the composition comprises a pharmaceutically acceptable excipient.

14. The method according to claim 12, wherein the psychedelic agent is the sole therapeutic agent of the composition.

15. The method according to claim 1, wherein the method comprises assessing the food allergy condition of the subject following the administering.

16. The method according to claim 1, wherein the subject is a mammal.

17. The method according to claim 16, wherein the mammal is a human.

18. The method according to claim 17, wherein the method further comprises psychotherapy before, during and/or after the administering.

* * * * *